US011622727B2

United States Patent
Lei et al.

(10) Patent No.: US 11,622,727 B2
(45) Date of Patent: Apr. 11, 2023

(54) PROCESS AND HARDWARE IMPLEMENTATION OF ADAPTIVE REAL-TIME NEURAL SPIKE SORTING

(71) Applicants: Tim Chifong Lei, Thornton, CO (US); Zeinab Mohammadi, Denver, CO (US); Achim Klug, Denver, CO (US); Chao Liu, Aurora, CO (US)

(72) Inventors: Tim Chifong Lei, Thornton, CO (US); Zeinab Mohammadi, Denver, CO (US); Achim Klug, Denver, CO (US); Chao Liu, Aurora, CO (US)

( * ) Notice: Subject to any disclaimer, the term of this patent is extended or adjusted under 35 U.S.C. 154(b) by 249 days.

(21) Appl. No.: 16/868,340

(22) Filed: May 6, 2020

(65) Prior Publication Data
US 2020/0352520 A1  Nov. 12, 2020

Related U.S. Application Data

(60) Provisional application No. 62/845,744, filed on May 9, 2019.

(51) Int. Cl.
*A61B 5/00* (2006.01)
*A61B 5/24* (2021.01)

(52) U.S. Cl.
CPC .............. *A61B 5/7264* (2013.01); *A61B 5/24* (2021.01); *A61B 5/40* (2013.01); *A61B 5/4064* (2013.01);
(Continued)

(58) Field of Classification Search
CPC ........ A61B 2503/40; A61B 2562/0209; A61B 5/24; A61B 5/40; A61B 5/4064;
(Continued)

(56) References Cited

U.S. PATENT DOCUMENTS 7,187,968 B2   3/2007   Wolf et al.
9,449,225 B2   9/2016   Ginosar et al.
(Continued)

FOREIGN PATENT DOCUMENTS

CA   2480132 A1   3/2006
WO   2007058950 A2   5/2007

OTHER PUBLICATIONS

Zeinab Mohammadi et al., Computationally inexpensive enhanced growing neural gas algorithm for real-time adaptive neural spike clustering, Journal of Neural Engineering, 2019, 16 056017.

*Primary Examiner* — Jon Eric C Morales

(57) ABSTRACT

Various methods and embodiments of the present technology generally relate to neural spike sorting in real-time. More specifically, some embodiments relate to a real-time neural spike sorting process using distributed nodes and edges to form clusters in the vector space to learn the neural spike data distribution adaptively for neural spike classification in real-time. The state of the brain or the onset of a neurological disorder can be determined by analyzing the neural spike firing pattern, and the first stage of the neural data analysis is to sort the recorded neural spikes to their originating neurons. Methods that can sort the recorded neural spikes in real-time with low system latency and can be implemented with resource limited digital electronic hardware, including a Field-Programming Gate Array (FPGA), an Application-Specific Integrated Circuit and an embedded microprocessor, are beneficial in understanding neuronal networks and controlling neurological disorders.

20 Claims, 17 Drawing Sheets

(52) U.S. Cl.
CPC ........ *A61B 5/6868* (2013.01); *A61B 2503/40* (2013.01); *A61B 2562/0209* (2013.01)

(58) Field of Classification Search
CPC ................ A61B 5/6868; A61B 5/7264; A61B 5/7267; A61B 2562/02; A61B 2505/00
See application file for complete search history.

(56) References Cited

U.S. PATENT DOCUMENTS

| | | |
|---|---|---|
| 9,717,440 B2 | 8/2017 | Abdelghani et al. |
| 2019/0000377 A1 | 1/2019 | Lei et al. |

EGNG nodes ($S_1$, $S_2$, and $S_3$) moving

New EGNG node adding

Ages of EGNG edge calculation

EGNG edges pruning

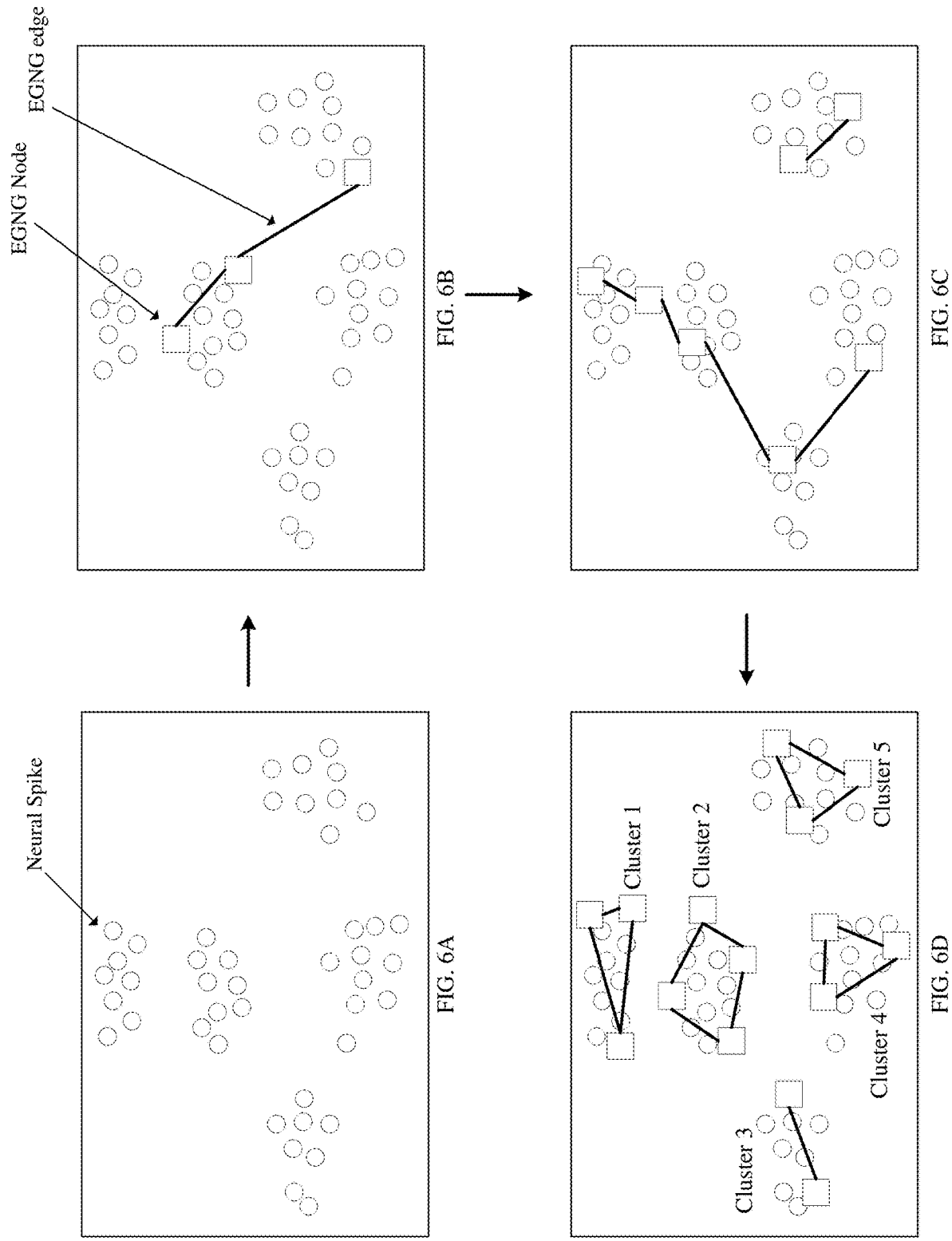

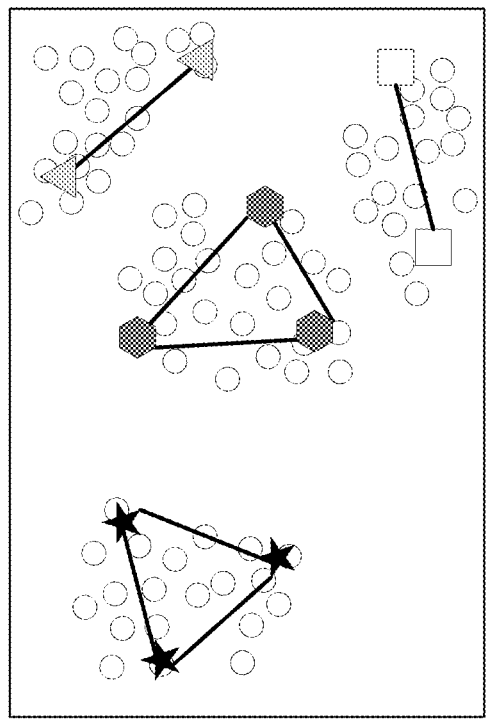
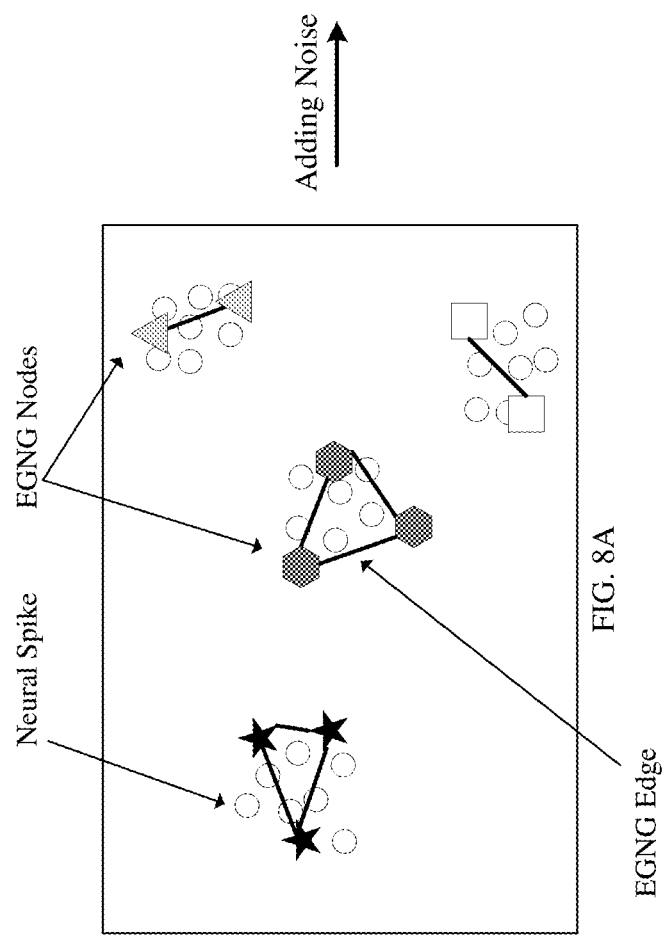
FIG. 8B
FIG. 8A

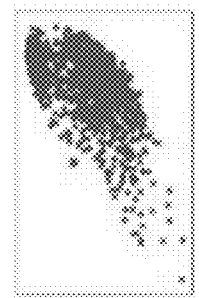
FIG. 13D
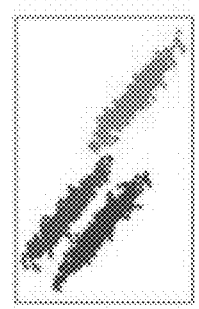
FIG. 13C
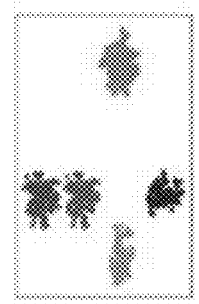
FIG. 13B
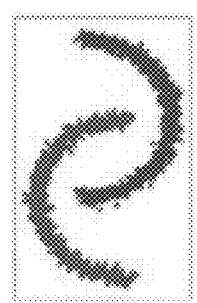
FIG. 13A
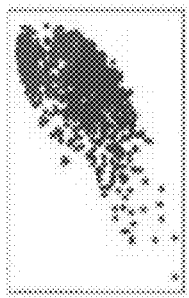
FIG. 13H
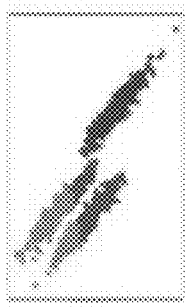
FIG. 13G
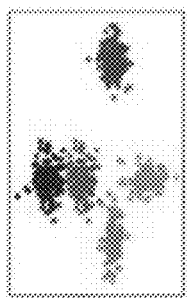
FIG. 13F
FIG. 13E
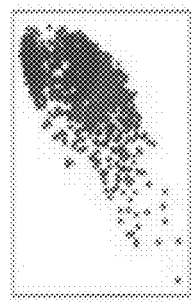
FIG. 13L
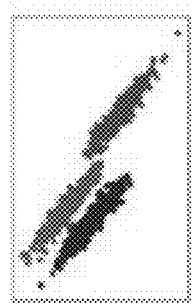
FIG. 13K
FIG. 13J
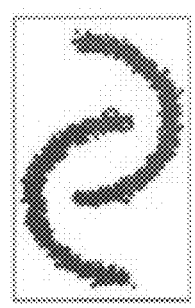
FIG. 13I
FIG. 13P
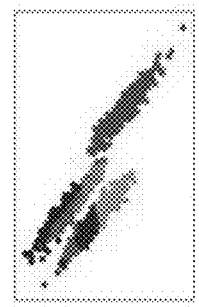
FIG. 13O
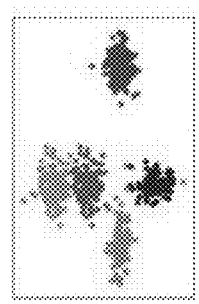
FIG. 13N
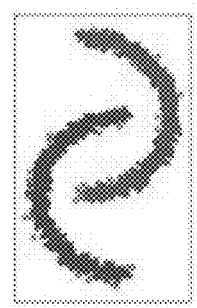
FIG. 13M
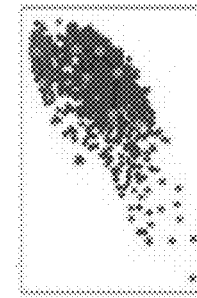
FIG. 13T
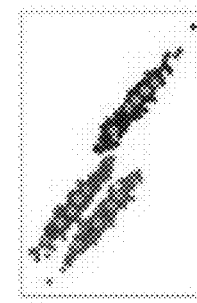
FIG. 13S
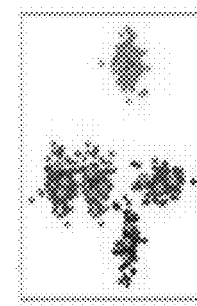
FIG. 13R
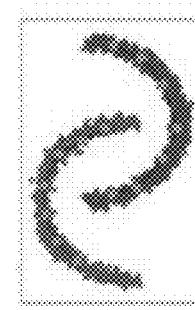
FIG. 13Q

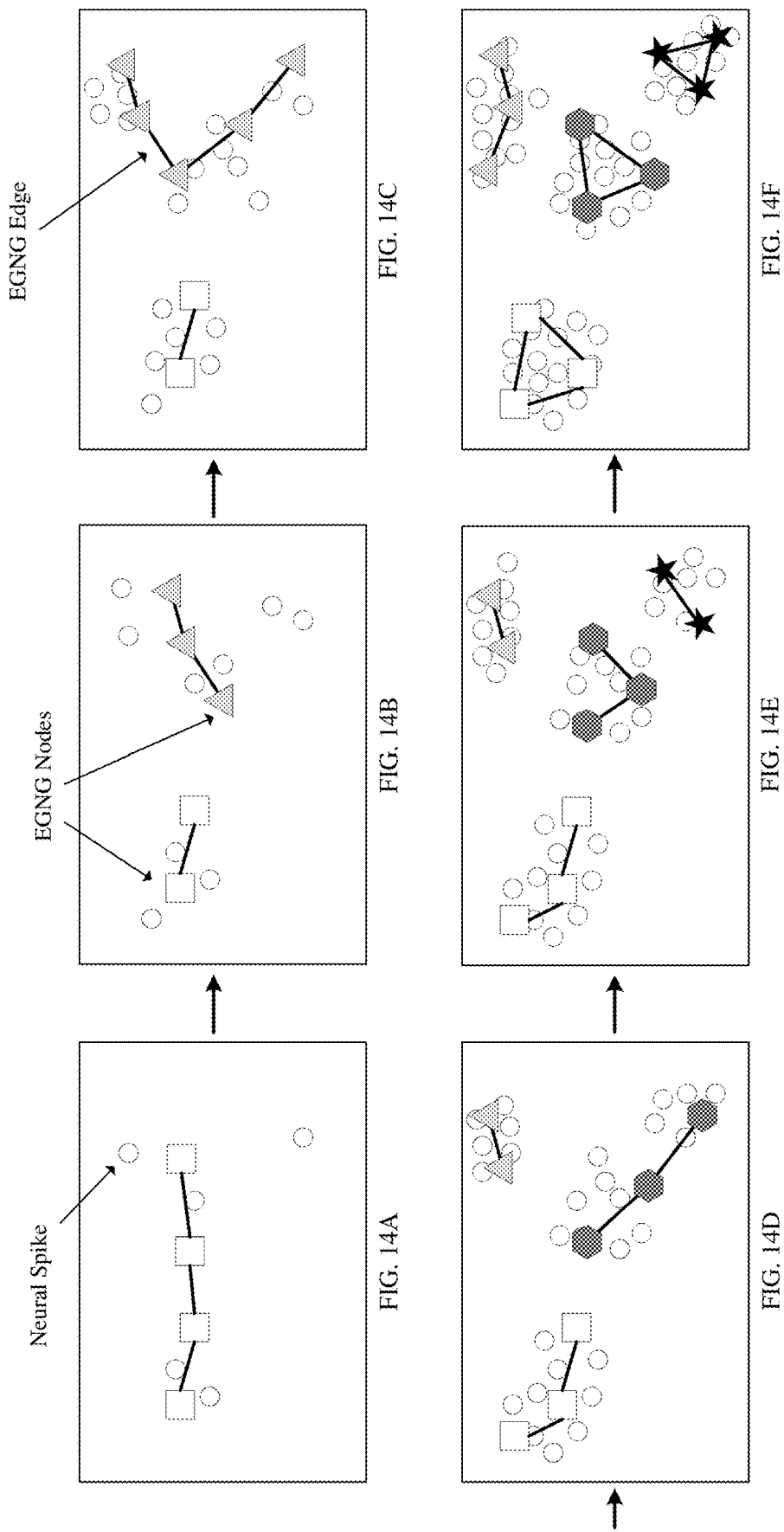

FIG. 15A
FIG. 15B
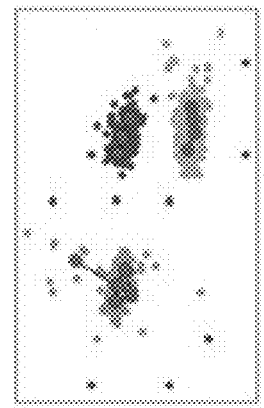
FIG. 15C
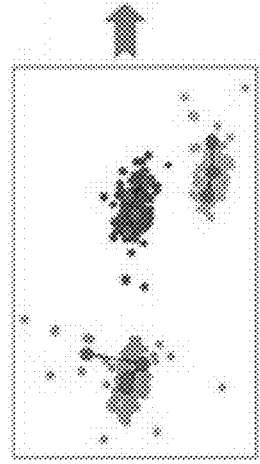
FIG. 15D
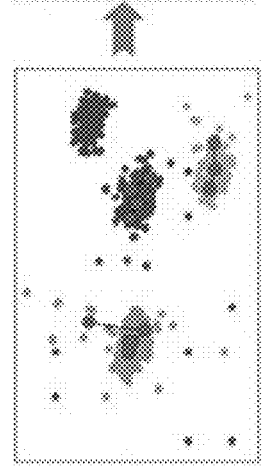
FIG. 15E
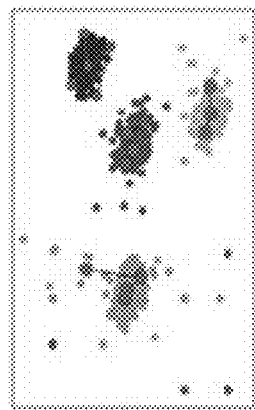
FIG. 15F
FIG. 15G
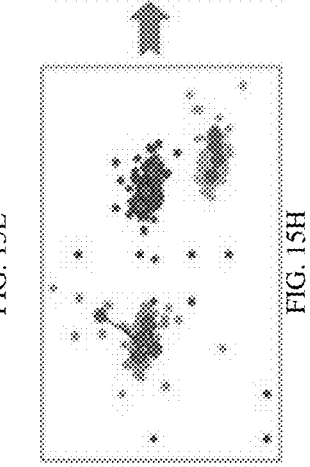
FIG. 15H
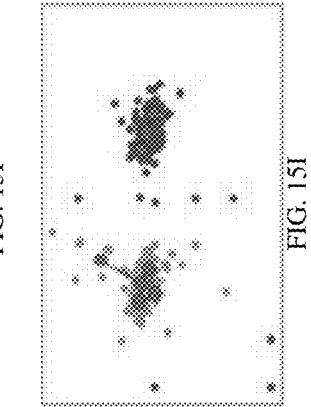
FIG. 15I
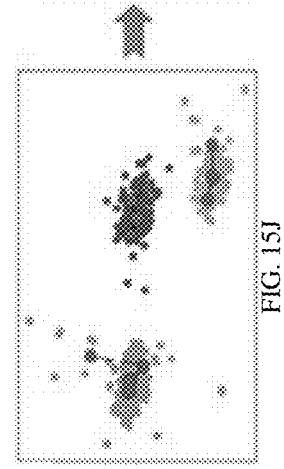
FIG. 15J
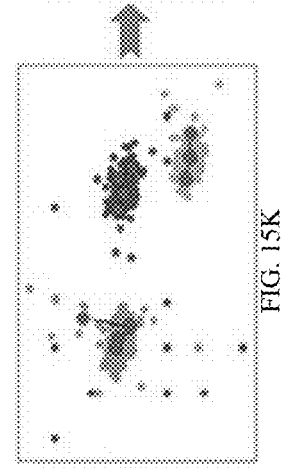
FIG. 15K
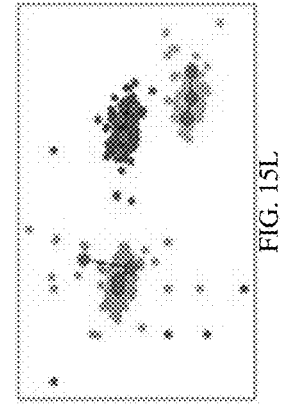
FIG. 15L

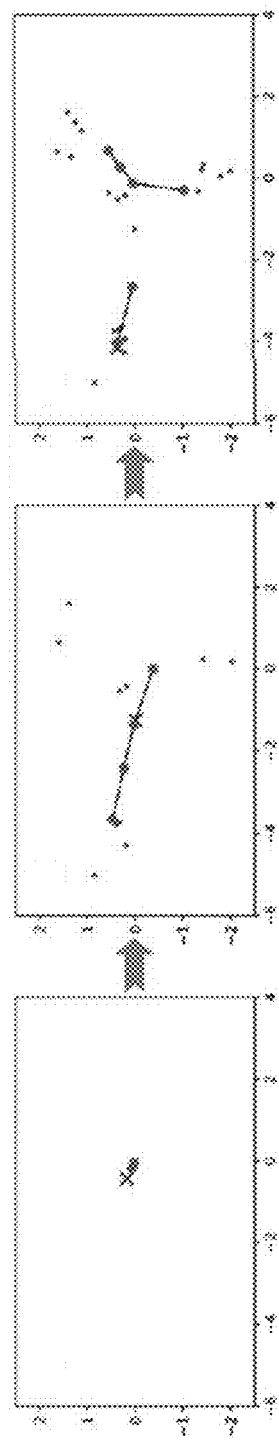
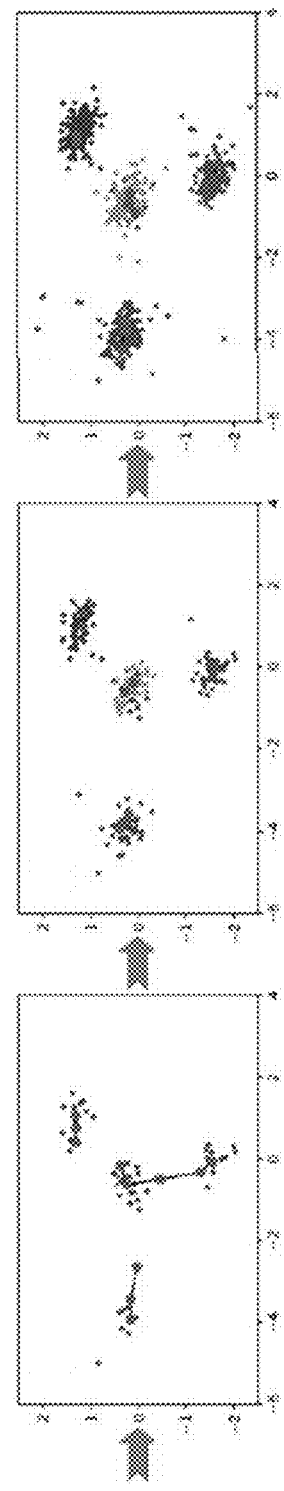
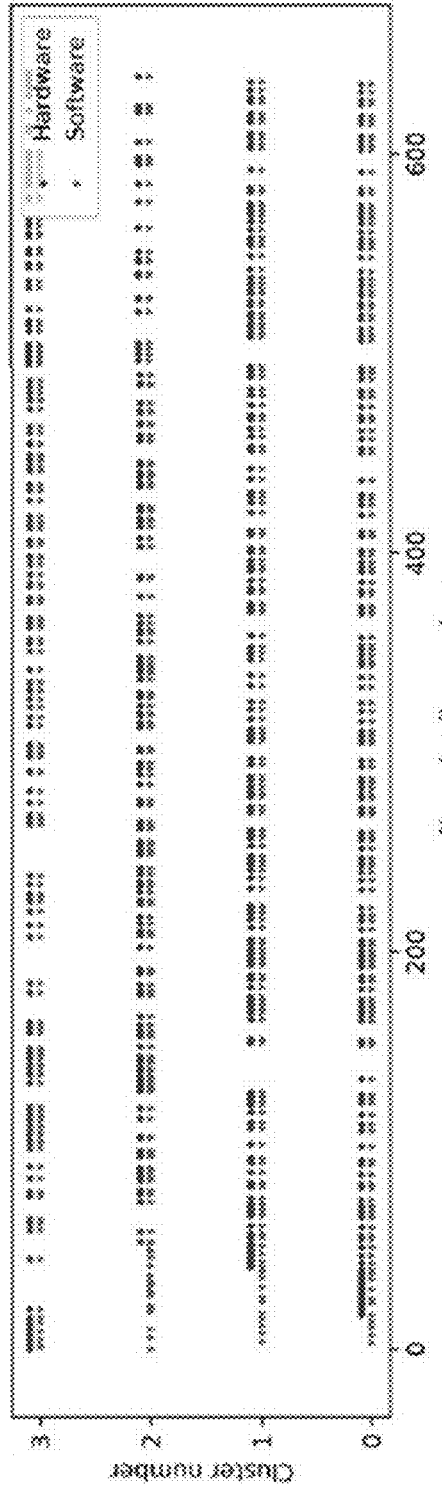
FIG. 16C  FIG. 16D  FIG. 16E
FIG. 16F  FIG. 16G  FIG. 16H
FIG. 16I ions in which 60 mine the state of the brain or the neural circuit and to# PROCESS AND HARDWARE IMPLEMENTATION OF ADAPTIVE REAL-TIME NEURAL SPIKE SORTING

CROSS-REFERENCE TO RELATED APPLICATIONS

This United States patent application claims priority to U.S. Provisional Patent Application 62/845,744 that was filed on May 9, 2019 and is entitled "PROCESS AND HARDWARE IMPLEMENTATION OF ADAPTIVE REAL-TIME NEURAL SPIKE SORTING." U.S. Provisional Patent Application 62/845,744 is hereby incorporated by reference into this United States patent application.

TECHNICAL FIELD

Various methods and embodiments of the present technology generally relate to neural spike sorting both off-line and in real-time. More specifically, some embodiments relate to a real-time neural spike sorting process using distributed nodes and edges to form clusters in the vector space to learn the neural spike data distribution adaptively for neural spike classification in real-time. In some embodiments, a hardware implementation of the adaptive spiking sorting process is realized.

BACKGROUND

Neurons are specialized cells in the brain which are interconnected to form large and complex neural networks to process and respond to the enormous information involved in operating both the human brain and animal brains. Neurons have a special biomolecular mechanism to generate neural spikes (action potentials) for information representation. Therefore, decoding information represented by neural spikes is one of the most important approaches to understand the state of the brain, the functioning of neural networks, and potentially also the onset of neurological disorders. Most commonly, neural spikes are measured with electrodes that are placed into the brain near neurons to obtain extracellular recordings. With this technique and depending on the exact location of the electrode relative to the surrounding neurons, a single recording site of a single electrode can often measure neural spikes from multiple neurons simultaneously if these are in close proximity to each other. In order to obtain the activity profile of a single neuron, it is necessary to "sort" or classify neural spikes into different groups that each represent neural activity from one single neuron only. This sorting can be done based on the temporal shapes of the recorded action potentials, which systematically differ between neurons in the recording. Once sorted, these neural spikes are associated with their originating neurons for further neural signal decoding. Over the last years, many different neural spike sorting processes were developed. Importantly, most of these processes were limited to sort previously recorded neural activity offline. Those few processes which can be used in real time require large computing resources (processing speed, memory, and energy) which limits their application to situations in which a full-sized external computer can be connected to the recording electrode. In order to respond quickly and in real time to ongoing patterns of neural activity, developing techniques to sort neural spikes rapidly and real-time is a critical requirement. Such real time spike sorting is necessary both for advanced neuroscience experimentation where an investigator might want to quickly respond to changes of brain state, but also for medical interventions where the detection of the onset of a pathological event such as a stroke or a seizure needs to be detected rapidly and reliably. Additionally, the electrophysiological environment around an electrode tends to drift over time, as the brain shifts. Therefore, real-time neural spike sorting techniques should also be adaptable to such changes in order for spike sorting to remain accurate and reliable during long-term neural recordings. Finally, the sorting process should be computationally "lightweight", i.e. require only small computational resources to function in real-time to allow for system miniaturization and the development of very small and energy efficient long-term neural implants.

SUMMARY

Enhanced Growing Neural Gas (EGNG) circuitry associates a neuronal spike with a cellular neuron. The EGNG circuitry comprises sensor circuitry and processing circuitry that are coupled together. The sensor circuitry senses a neuronal signal that was generated by the cellular neuron and that indicates the neuronal spike and transfers the neuron signal. The processing circuitry receives the neuronal signal from the sensor circuitry, assigns the neuronal spike to a point in a vector space, and assigns EGNG nodes to other points in the vector space. The processing circuitry determines distances from the EGNG nodes to the neuronal spike and identifies a set of closest ones of the EGNG nodes to the neuronal spike. The processing circuitry connects the set of closest one of the EGNG nodes with one or more EGNG edges. The processing circuitry modifies the other points of the EGNG nodes to reduce the distances between the neuronal spike and the set of the closest ones of the EGNG nodes. The processing circuitry adds one or more new EGNG nodes to the vector space when the distances fall below a distance threshold and responsively deletes the one or more EGNG edges. The processing circuitry adds one or more new EGNG edges between the new EGNG node and the set of closest ones of the EGNG nodes. The processing circuitry associates the neuronal spike with the cellular neuron based on the one or more new EGNG edges and transfers output data that indicates the cellular neuron in association with the neuronal spike.

BRIEF DESCRIPTION OF THE DRAWINGS

Embodiments of the present technology will be described and explained through the use of the accompanying drawings in which:

FIG. 6A illustrates how the EGNG process can be used to sort neural spikes in off-line mode on artificially generated neural points simulating neural spikes generated from five different nearby neurons.

FIG. 6B illustrates three EGNG nodes (white square) were interconnected by two EGNG edges (black line) at the beginning of the process.

FIG. 6C illustrates how more EGNG nodes were generated to distribute across the entire spectrum of neural data. Edge pruning has also occurred to separate an EGNG cluster from the main EGNG tree.

FIG. 6D illustrates the final results in an example where five EGNG clusters were formed and the neural points were classified by identifying the nearest EGNG node.

FIG. 8A is an example of classifying loosely spaced neural groups by the EGNG process.

FIG. 8B illustrates an example of how the EGNG process can be used to still reliably separate closely spaced neural groups when normally distributed noise was artificially added to the four neural groups.

FIGS. 13A-13D are the sorting results of four different neural datasets: A) synthetic noisy moon data, B) synthetic five cluster groups with Gaussian distribution, C) synthetic three cluster groups with anisotropic Gaussian distribution, and D) actual pre-recorded real neural spikes from a gerbil. The results were classified by the Density-Based Spatial sorting of Applications with Noise (DBSCAN) process.

FIGS. 13E-13H are the sorting results of four different neural datasets using the K-means process.

FIGS. 13I-13L are the sorting results of four different neural datasets using the Expectation Maximization (EM) process.

FIGS. 13M-13P are the sorting results of four different neural datasets using Super-paramagnetic sorting (SPC) process.

FIGS. 13Q-13T are the sorting results of four different neural datasets using the EGNG process. The EGNG process is the only process that can correctly classify all four datasets while the other three processes have trouble classifying at least one of the data sets.

FIG. 14A is an example illustrating how the EGNG process can be used to sort streaming neural spikes in real-time. At the beginning of the sort, a few neural points were streamed into the system and several connected EGNG nodes were created forming a single EGNG cluster. Since only one EGNG cluster was formed, all the neural points were classified to the cluster (white circle).

FIG. 14B illustrates how the EGNG nodes break into two clusters as more neural points are streamed in. New incoming neural points will be classified based on the shortest Euclidian distances to the two clusters (cluster 1—white square, left; cluster 2—gray triangle, right).

FIG. 14C illustrates how neural points are classified to the two EGNG clusters as the EGNG nodes are learning the neural data distribution.

FIG. 14D illustrates that the EGNG nodes are further broken into three groups and new incoming neural points are classified into three cluster groups (cluster 1—white square, left; cluster 2—gray triangle, above; cluster 3—dark gray hexagon, right).

FIG. 14E illustrates that the EGNG nodes are broken into four groups as the data distribution becomes more apparent, as more data are analyzed. New incoming data were classified into four clusters (cluster 1—white square, left; cluster 2—gray triangle, above; cluster 3—dark gray hexagon, center; cluster 4—black star, right).

FIG. 14F is the final EGNG cluster distribution after the neural data distribution has been learned by the process. The EGNG clusters become stable and new incoming neural data are correctly classified into four groups.

FIGS. 15A-15C illustrates that the EGNG process is highly adaptive to changes in neural distribution. Three stable EGNG clusters were initially established and new neural points were added to the left side of the lower cluster. EGNG nodes were moved to the left to adapt to the movement of the new data distribution.

FIGS. 15D-15F illustrates how the EGNG process can add a new EGNG cluster to a newly recorded neuron. Neural points (grey) are added to the upper left side to simulate a new neuron being recorded and a new EGNG cluster was created to correctly classify the new neural spikes.

FIGS. 15G-15I illustrates the deletion of obsolete clusters. No neural points near that EGNG cluster were put into the process to simulate the drop-out of neural spikes from a neuron which can no longer be picked up by the electrode. The EGNG cluster covering these original neural points is eventually removed from the distribution.

FIGS. 15J-15L illustrates noise rejection by the EGNG process. Neural points far away from the clusters are classified as noise and rejected.

FIGS. 16C to 16H illustrate the real-time neural spike classification using the FPGA hardware with streaming neural data.

FIG. 16I is the semi-raster plot comparing the classification between the software and hardware implementations.

DETAILED DESCRIPTION

Various embodiments of the present technology generally relate to real-time neural spike sorting. More specifically, some embodiments relate to sort neural spikes based on the Enhanced Growing Neural Gas (EGNG) process in which EGNG nodes are used to learn the neural data distribution, and the EGNG nodes interconnecting to form clusters to classify neural data based on the shortest Euclidian distance between the data point and the EGNG nodes. In some embodiments, the EGNG process can be used to sort pre-recorded neural spikes in off-line mode. In other embodiments, the EGNG process can be used to sort real-time streaming neural spikes. The EGNG clusters can be moved, added, and deleted to correctly sort neural spikes as the electrophysiological conditions change, especially in long term neural recordings. In some embodiments, the process can be implemented using digital electronic hardware, such as a Field Programmable Gate Array (FPGA), an Application Specific Integrated Circuit (ASIC) or an embedded microprocessor. In some embodiments, the process can be implemented as a hardware system to sort neural spikes to their respective originating neurons. In some embodiments, the process can be implemented as the front-end hardware to sort neural spikes for downstream neural data analysis and to use the analyzed results to control neural circuits in a closed-looped manner.

Figure 1:
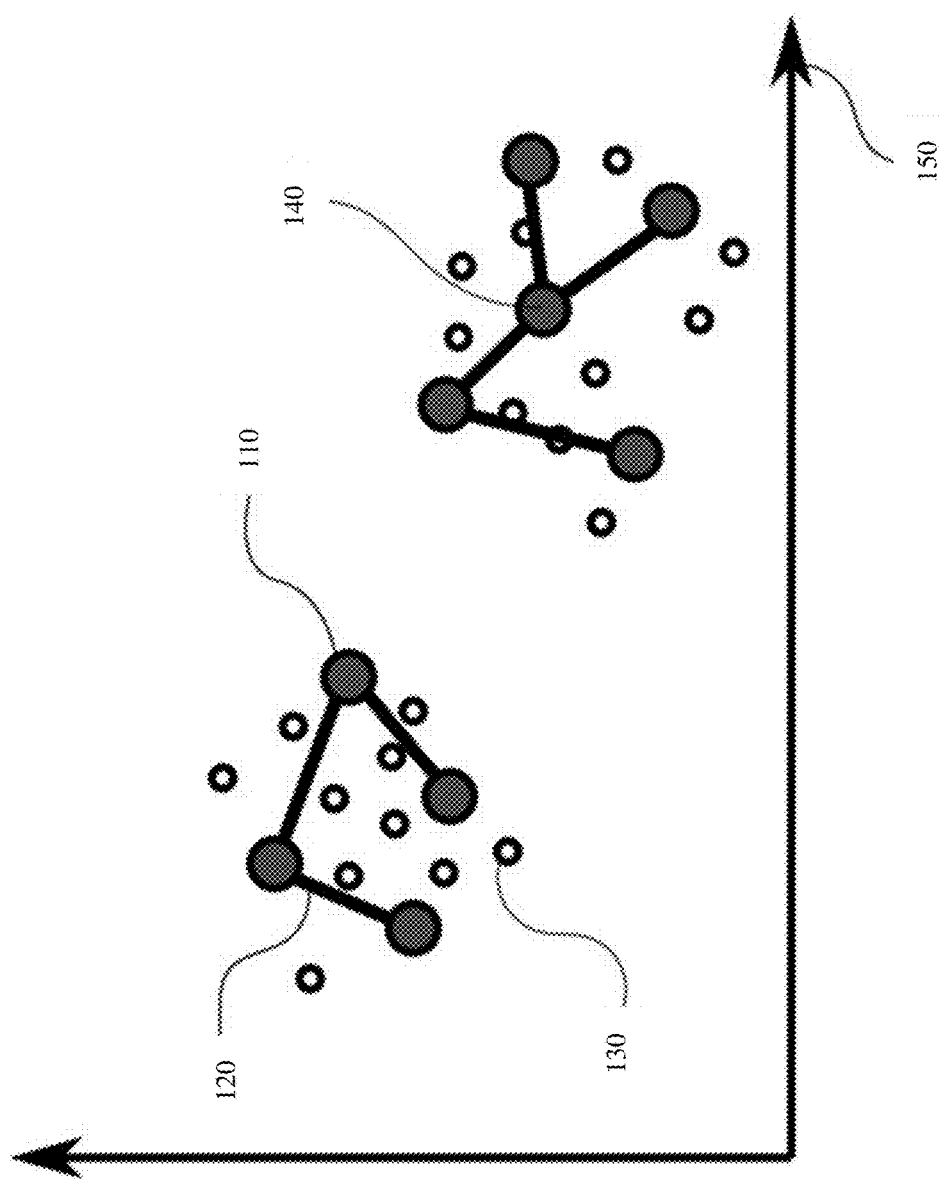
FIG. 1 illustrates the major components and the axes of the vector space in the Enhanced Growing Neural Gas (EGNG) process to classify neural spikes.

FIG. 1 illustrates the major components of the EGNG process. EGNG nodes 110 are distributed mathematical nodes in the vector space 150 interconnected by EGNG edges 120 to form EGNG clusters 140. Incoming neural spikes 130 are converted into mathematical points in the vector space 150 based on signal transformation techniques such as principal component analysis (PCA), wavelet transform, Fourier transform, Laplace transform, or the like. The EGNG nodes 110 and EGNG edges 120 are then used to learn the distribution of the neural spikes 130 to form EGNG clusters 140. In some embodiments, the EGNG process can be directly performed in the time domain with the needs of signal transformation or dimensional reduction.

Figure 2:
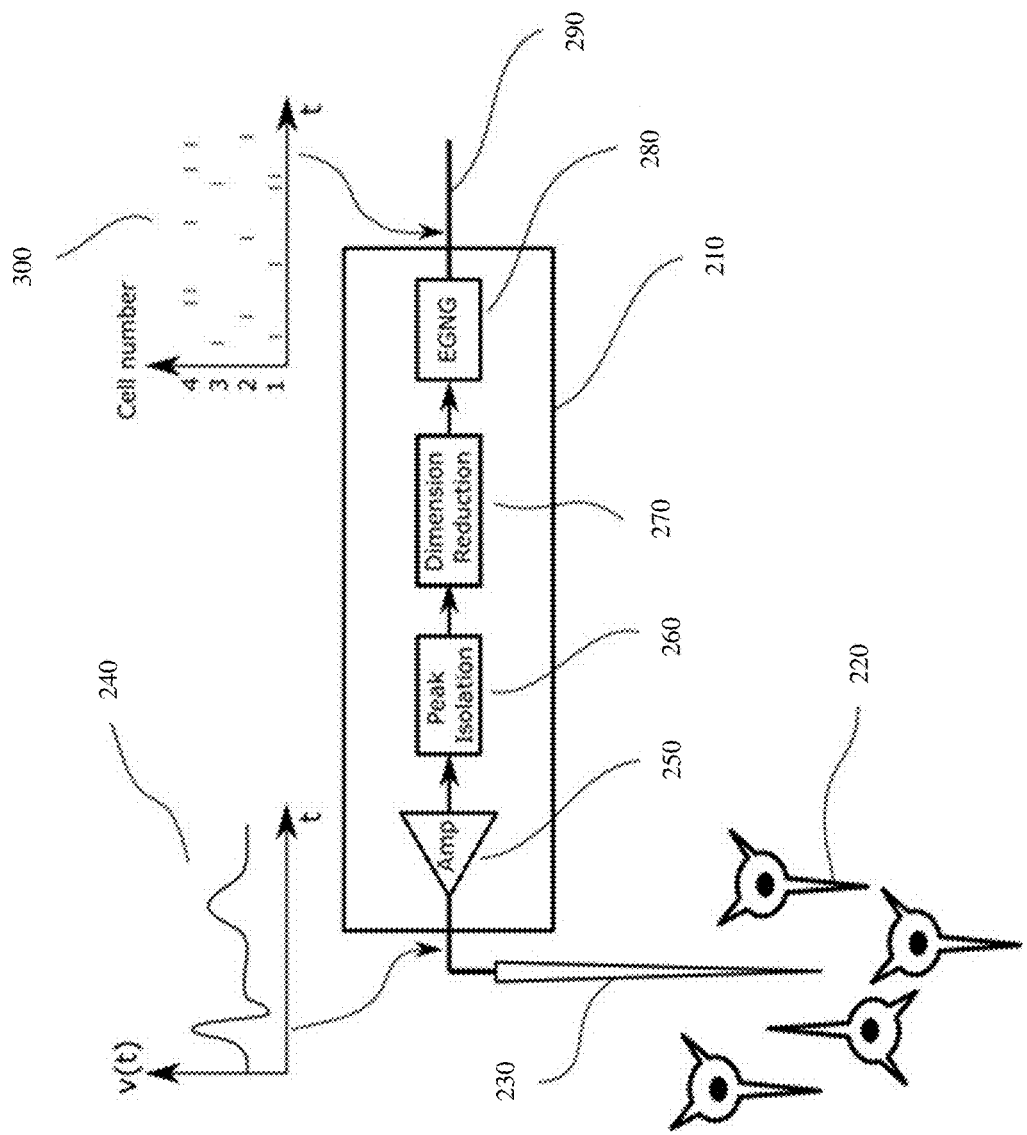
FIG. 2 illustrates an embodiment of how the EGNG process can be hardware implemented to classify neural spikes to generate a raster plot in a real-time neural recording scenario.

In some embodiments, the EGNG process is implemented as a hardware module 280 using digital electronic technologies such as FPGA, ASIC, and an embedded processor, as shown in FIG. 2. An electrode 230 is placed surgically within the brainnear some neurons 220. Neural spikes fired by these neurons 220 are then picked up by the electrode 230 and measured by an amplifier 250. The amplifier 250 measures the neural spikes and converts them as a time trace 240 containing neural spikes with different temporal waveforms according to the relative positions and the proximities between the originating neurons and the electrode. A peak isolation module 260 detects the peaks of these waveforms and isolates them from the recorded voltage trace 240 into individual waveforms. An optional dimension reduction module 270 can be implemented to transform the isolated neural spikes into points and also reduce the dimensions of the points in the vector space. The neural points are then put into the EGNG module 280 for spike sorting. The EGNG module 280 then generates a raster plot 300 plotting the event time of the neural spikes. The same module also categorizes the neural spikes into groups each of which represents firing from a single neuron, and send this information to the output 290. In some embodiments, the amplifier 250, the peak isolation module 260, the dimension reduction module 270 and the EGNG module 280 can be integrated into a miniaturized integrated circuit (IC) chip and a miniaturized computer system 210. In some embodiments, the recording electrode 230 may have more than one recording site and the system 210 may have multiple modules to parallel—process the neural spikes recorded at the different sites.

Figure 3:
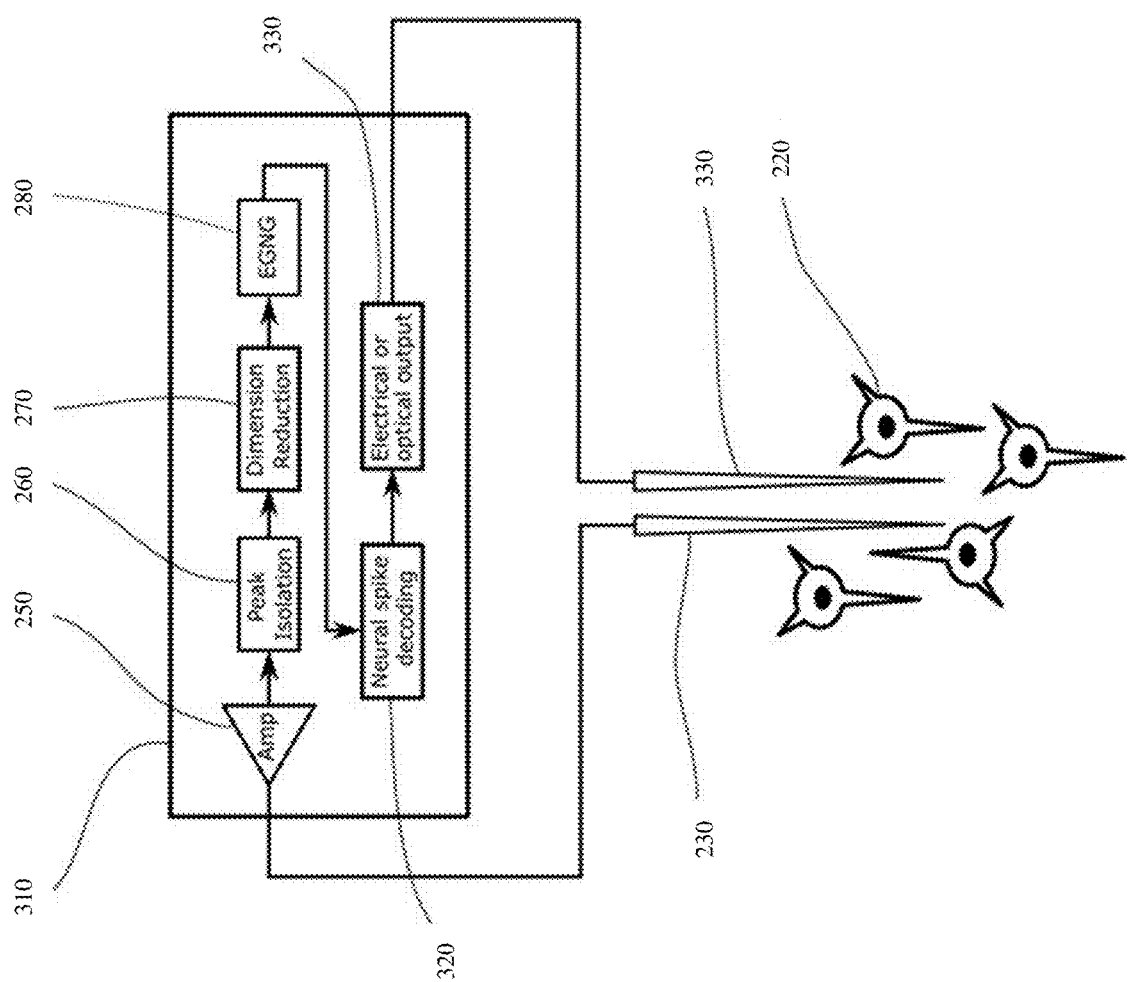
FIG. 3 illustrates an embodiment of how the EGNG process can be hardware implemented and integrated in a closed-loop neural recording and control system to determine the state of the brain or the neural circuit and to intervene it electrically or optically.
Figure 4A:
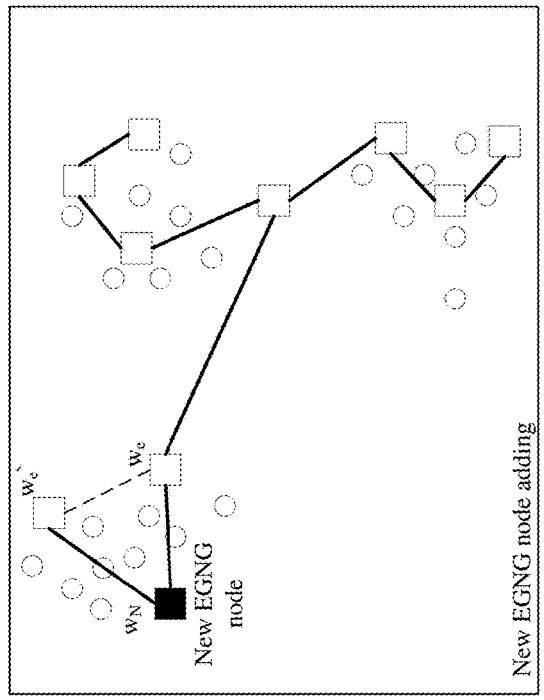
FIG. 4A illustrates the EGNG process for sorting pre-recorded neural spikes off-line near the beginning of the sorting process. A few EGNG nodes were generated and connected by EGNG edges. The closest EGNG node ($S_1$) and its neighboring nodes moved closer to a neural point ($x_i$) with different movement rates.
Figure 4B:
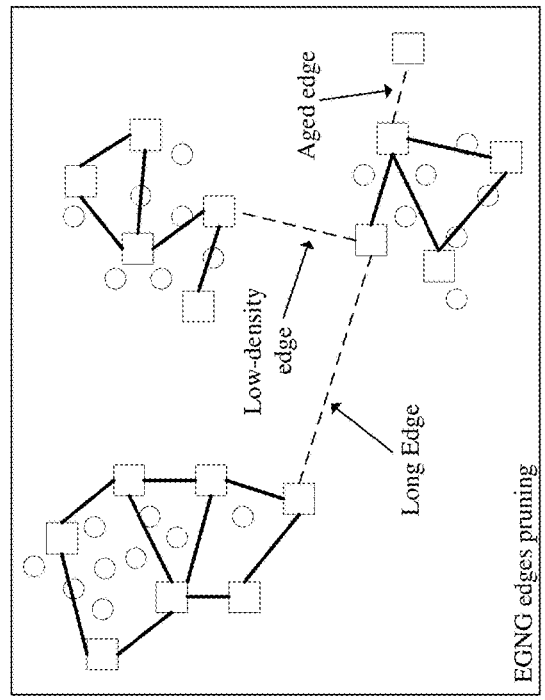
FIG. 4B illustrates how a new EGNG node ($S_1$) is inserted between the node with the largest insertion value ($inserts_e$) $S_e$ and its closest neighboring EGNG node ($S_{e'}$) during the sorting process.
Figure 4C:
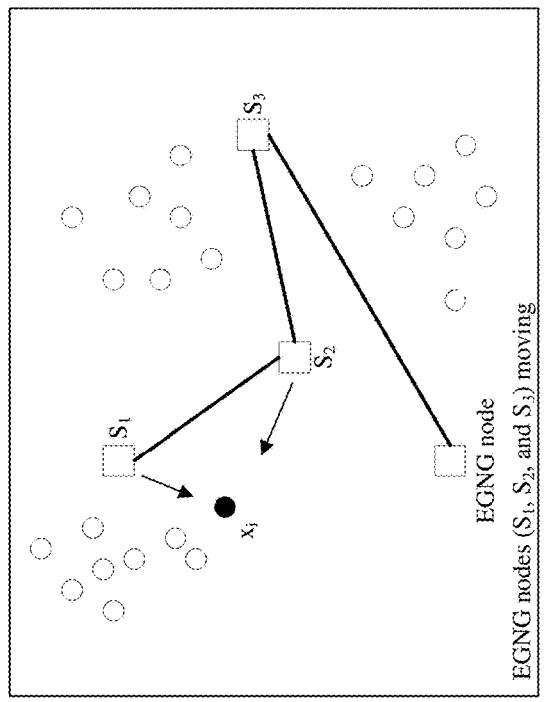
FIG. 4C illustrates how the age parameters are calculated.
Figure 4D:
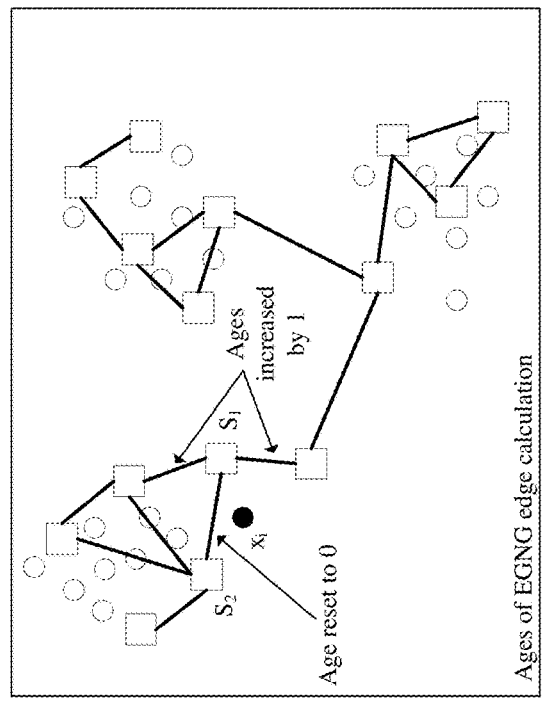
FIG. 4D illustrates when the age of an edge reaches the age threshold ($\alpha > \alpha_{th}$), and the aged edge is pruned.

In some embodiments, the EGNG process can be implemented as a hardware module 280 to be integrated in a closed-looped neural recording and control system 310, as shown in FIG. 3. A recording electrode 230 is used to record neural spikes from a group of neurons 220 in the proximity of the recording electrode. An amplifier 250 is used to record the neural spike voltage, followed by a peak isolation module 260 to detect and isolate the neural spikes as individual voltage traces. An optional dimension reduction module 270 is used to transform the neural spikes in the temporal domain into neural points at the vector space and further reduce the data dimensions. The EGNG module 280 is then used to sort the neural spikes into the originating neurons for subsequent data analysis. A neural spike decoding module 320 is used to determine the state of the brain using the sorted neural spikes. Several methods can be used to analyze the sorted neural spikes, including but not limited to thresholding of the firing rates, the arriving times of the neural spikes, linear or nonlinear classifiers such as support vector machines, naïve Bayesian classifications, Gaussian mixture models, and the like. An electrical current driver circuit or optical illumination driver circuit 330 is implemented as the final stage of the system 310 to output an electrical current or optical illumination for the purpose of exciting or to inhibiting neural activity in the brain tissue. In some embodiments, the output electrical or optical electrode 340 may be a separate electrode from the recording electrode 230 and may also be placed in a remote location. In some embodiments, the output electrical or optical electrode 340 may also be integrated into the recording electrode 230 as a single electrode to control the same or closely located neurons as the ones which provided the initial neural signal. In some embodiments, the modules in the closed loop recording and control systems 310 may be duplicated to handle neural spikes recording from multiple recording and stimulation sites of a multichannel electrode or several electrodes.

In some embodiments, the EGNG process may be used to sort pre-recorded neural spikes in off-line mode. Similar to other spike sorting processes, neural spikes measured in the time domain may be transformed onto a multi-dimensional vector space using techniques such as principal component analysis (PCA) or wavelet transformation. In this manner, neural spikes are transformed into neural points in a multi-dimensional vector space constructed by a chosen set of basis functions. Here the term "neural point" is defined as the feature vector in the vector space transformed from a neural spike in the time domain. Neural points with similar temporal spike profiles are consequentially clustered together into a group in the vector space. Therefore, the principle of the EGNG process is to cover these neighboring neural points with EGNG nodes and interconnect them with EGNG edges to form EGNG clusters. In this way, EGNG can be considered as a process of forming clusters using EGNG nodes and edges on top of the distribution of neural data, and to constantly adapt and follow changes of the data distribution in the vector space. In some embodiments, the transformation of the neural spikes to the vector space or reducing the dimensions of the data may be omitted by directly using the temporal data to form points.

In this off-line sorting configuration, neural spikes are pre-recorded and classified after the experiment has concluded. Consequentially, the EGNG process does not need to be limited in terms of computing resources. Both computing power and memory are considered abundant such that all the neural data points can be stored in the system memory for recursive processing. Note this is in stark contrast to a case in which streaming neural data are classified in real-time (see below). The parameters for the EGNG process and the values used in this paper for classification are listed in Table 1. Generally, only the maximum node count ($N_{EGNG}$) and the edge pruning threshold ($\alpha_{th}$) are sensitive to the classification results.

TABLE 1

Parameters of the EGNG process. The values used in the manuscript and the typical ranges of the parameters are listed.

| Parameters | Values used in this patent | Typical ranges |
| --- | --- | --- |
| Maximum node count ($N_{EGNG}$) | 10 to 15 for most dataset and 100 for ring dataset | 3 to Max (depends on the data) |
| Edge pruning threshold ($\alpha_{th}$) | 4 to 8 for most dataset and 30 for ring dataset | A fraction of total node count (e.g. half or one-third). |
| Number of initial nodes (N) | 2 | 2 |
| Moving rate pf $S_1$ ($e_{s_1}$) | 0.1 | (0, 1) |
| Moving rates of $S_1$ ($e_{nbr}$) | 0.006 | (0, 1), $e_{s_2} > e_{nbr}$ |
| Insert parameter reduce rate of $w_e$ and $w_e^1$ nodes ($\alpha$) | 0.5 | (0, 1) |
| Insert parameter reduce rate of other nodes ($\beta$) | 0.01 | (0, 1) |
| Number of iterations before inserting a new node ($\lambda$) | 10 | 5 to 50 |

The steps for off-line EGNG to classify pre-recorded neural spikes are illustrated in FIGS. 4A-4D.

1) Initialization: Several EGNG nodes connected by EGNG edges are randomly generated and placed among the neural data in the vector space. The locations of the EGNG nodes are denoted as wj and the number of EGNG nodes created is denoted as N.

2) Finding the closest EGNG node: A neural point $x_i$ is randomly selected among the entire neural data distribution. The Euclidian distances ($dj=|x_i-W_j|$) between the selected neural data point ($x_i$) and all the EGNG nodes ($W_j$) are then calculated. The EGNG nodes with the shortest and second shortest Euclidean distances are denoted as $S_1$ and $S_2$.

$$S_1 = \mathrm{argmin}_{wj \in N}(d_j)$$

$$S_2 = \mathrm{argmin}_{wj \in N \setminus \{S_1\}}(d_j)$$

If the two closest EGNG nodes ($S_1$ and $S_2$) have not been connected by an EGNG edge, a new EGNG edge is constructed to connect them.

3) Moving the closest EGNG node and its neighboring nodes closer to the neural point $x_i$: A neighboring node is another EGNG node that connects to an EGNG node directly by an EGNG edge, without another EGNG node crossed in between. In this step, $S_j$ are denoted as all the neighboring nodes to the closest EGNG node ($S_1$). $S_1$ and all $S_j$ are moved closer towards the neural data point (xi), but with different movingrates.

$$S_1 \leftarrow S_1 + e_{s_1}(x_i - S_1)$$

$$S_j \leftarrow S_j + e_{nbr}(x_i - S_j)$$

where $e_{s1}$, $e_{nbr} \in (0,1)$ are the moving rates of $S_1$ and $S_j$, where $e_{s1} > e_{nbr}$. An "Insertion" parameter ($\mathrm{insert}_{wi}$) is used to determine where a new EGNG node should be inserted. After $S_1$ has moved toward $x_i$, $\mathrm{insert}_{s1}$ is increased by $$\mathrm{insert}_{s1} \leftarrow \mathrm{insert}_{s1} + \|x_i - S_1\|^2$$

4) Insertion of a new EGNG node using the insertion parameter: If the number of total EGNG nodes is less than the maximum node count (NEGNG), a new EGNG node is added after λ iterations. The EGNG node with the highest insertion and one of its neighbors with the highest insertion among all the neighboring nodes will be identified, and the positions of the two EGNG nodes are denoted as we and we'. The position of the new EGNG node (wN) is equal to $$W_N = \frac{1}{2}(W_e + W_{e'})$$

EGNG will prune the EGNG edge connecting $W_e$ and $W_{e'}$, and will create two new EGNG edges connecting between $W_e$ and $W_N$ and between $W_{e'}$ and $W_N$. After the insertion, the insertion parameters of the two nodes are reduced to avoid repetitive EGNG node creation, $$insert_{w_e} \leftarrow \alpha \cdot insert_{W_e}$$

$$insert_{w_{e'}} \leftarrow \alpha \cdot insert_{W_{e'}}$$

$$insert_{W_N} insert_{W_e}$$

In addition, the insertion parameters of all the other EGNG nodes are reduced by β, where α, β∈(0,1) are the insertion reduction rates.

5) Edge pruning with the age parameter: If the EGNG edge is spanning over an area with few neural points, the EGNG edge will be removed to allow cluster separation. In order to allow pruning, an "age" parameter ($\alpha_k$) is assigned to all EGNG edges to determine if an EGNG edge should be pruned. For the EGNG edge connecting ($S_1$ and $S_2$), the age ($\alpha s_1$, $S_2$) of this edge is reset to zero, indicating this edge is close to the neural point (xi) and the EGNG edge should be retained.

$$\alpha_{s_1, S_2} \leftarrow 0$$

However, for other neighboring EGNG edges connecting $S_j$ to $S_1$, the ages ($a_{s1}$, $S_j$) of these edges are increased by 1, indicating that these edges are farther away from the neural point ($x_i$), leading to a higher chance of eventually being pruned.

$$\alpha_{s_1, S_j} \leftarrow \alpha_{S_1, S_j} + 1$$

With this strategy, the ages of remote EGNG edges will be increased steadily. When the age of an edge is higher than the edge pruning threshold ($\alpha_{th}$ ($\alpha_{Si}$, $S_j > \alpha_{th}$)), the EGNG edge is pruned to allow cluster separation.

6) Termination criteria: After all the neural points have been processed and if the number of EGNG nodes (N) created is less than the maximum node count ($N_{EGNG}$), the neural points will be processed one more time to allow all the EGNG nodes to be generated for better sorting. After all the EGNG nodes are generated, the EGNG sorting will be terminated. This termination criteria generally results in well-separated EGNG clusters if the neural clusters are far from one another and the neural points are densely clustered in the cluster centers. However, if the neural clusters are close to one another and the cluster centers are not densely packed, this termination criteria are not strong enough to ensure sufficient separation between neural clusters. For this reason, two strategies—removing long edges and removing low-density edges—are used to allow the EGNG process to better separate the neural clusters even if they are loosely packed and close to one another. Closely packed and loose neural data distributions are common for actual electrophysiology recordings in animals.

(a) Removing long edges: The length of an EGNG edge is $l_{wi,wj} = |W_j - W_i|$. The EGNG edge is removed if its length ($l_{wi,wj}$) is larger than the average length of all the EGNG edges ($l_{ave}$), that is $l_{wi, wj} > l_{ave}$.

(b) Removing low-density edges: The average Euclidian distance of five neural points closest to the middle point of an EGNG edge is calculated as $l_{mid}$, and $\overline{l_{mid}}$ is the average $l_{mid}$ of all the EGNG edges. An EGNG edge is considered as a low-density edge and needed to be removed if $l_{mid} > \overline{l_{mid}}$.

Pseudo-code of the off-line EGNG process to sort pre-recorded neural spikes is listed below:

---
Process 1: Offline EGNG implementation
---

```
While (the number of inserted nodes < Predefined Number of nodes) and (stopflag = 1)
    For each training epoch
        For each datapoint in dataset (x_i)
            Calculate the distance between existing nodes (w_j) and the new datapoint
                d_j = ||x_i - w_j||
            Choose two nodes with lowest distances
                S_1 = argmin_{w_j∈N} (d_j)
                S_2 = argmin_{w_j∈N\{S_1}} (d_j)
            Set the connection of S_1 to S_2 to zero
            Update the location of S_1 and its topological neighbors (S_j) using learning rates
                S_1 ← S_1 + e_{s_1} (x_i - S_1)
                S_j ← S_j + e_{nbr} (x_i - S_j)
            Update the accumulated error ("insert" parameter) of S_1 as
                insert_{s_1} ← insert_{s_1} + ||x_i - s_1||^2
        Increase the age of all edges connected to S_1
        If the number of inserted nodes > 2 (initial stage has passed)
            If each edge > Edge removal threshold
                Remove that edge
            If there is a node without any connection
                Remove that node and its location and insert parameters
                Decrease all error variables using Decreasing rate (β)
        If the number of inserted nodes < Predefined Number of nodes
            Determine node w_e with the largest 'insert' parameter
            Determine the node with the largest error w_{e'} among the connected nodes to w_e
            Insert a new node w_N between two we' and we nodes as
                w_N = 0.5(w_e + w_{e'})
        Remove the edge between we' and we
        Connect new node w_N to w_{e'} and w_e by making two edges
        Decrease insert parameters of nodes w_{e'} and w_e by an error rate (α)
            insert_{w_e} ← α · insert_{w_e}
            insert_{w_{e'}} ← α · insert_{w_{e'}}
```

Process 1: Offline EGNG implementation

Set new node $w_N$ insert parameter as
    $insert_{w_N} \leftarrow insert_{w_e}$
  Set new node $w_N$ insert parameter as
    $insert_{w_N} \leftarrow insert_{w_e}$
To remove long edges that connected several clusters
  Calculate all EGNG edges length as
    $l_{w_i,w_j} = \|w_j - w_i\|$
  Calculate the average of these edges' length (threshold)
    $l_{ave} = \text{mean}(l_{w_i,w_j})$
  For all EGNG edges length
    If $l_{w_i,w_j} > l_{ave}$
      Prune $l_{w_i,w_j}$
    Set stopflag = 0 to show that this stage of edge removing finished
To remove low-density edges
  For every edge in EGNG
    Calculate the Euclidian distances of five data points (closest to the middle of an EGNG edge) and the middle point location of that edge
    Calculate the average of these five distances and consider it as a label number for that edge ($l_{mid}^i$)
  Calculate the average of all $l_{mid}^i$ (threshold)
    $\overline{l_{mid}} = \text{mean}(l_{mid}^i)$
  For every edge in EGNG
    If $l_{mid}^i > \overline{l_{mid}}$
      Remove the edge as it is in a very low-density area (between clusters area)

In some embodiments, the EGNG process can be used to sort streaming neural spikes in on-line mode to classify streaming neural spikes rapidly and accurately with limited processing power and memory. The limited use of computational power and memory allow hardware miniaturization to fit all the necessary circuits into a small FPGA or ASIC to avoid cable tethering to a main computer. Another benefit of rapid spike sorting is that it may enable immediate neural decoding such that the decoded information can be used to drive closed-loop neural feedback control, such as optogenetic stimulation or inhibition. Unlike off-line EGNG where all neural points are stored in the memory and processed recursively, real-time EGNG does not retain the neural points in the memory once they are processed. Instead, EGNG learns the cluster distribution from the neural points and only stores the learned distribution into the EGNG node positions and edge connections. This approach is similar to Bayesian inference in which the streaming of neural points serves as priors, and the EGNG clusters will approximate the neural data distribution as more and more spikes are streamed in and processed resulting in more accurate classifications for subsequent neural spikes. FIGS. 5A-5F illustrate the process of on-line EGNG, as well as showing how the process can adapt to changes of the neural data distribution dynamically.

Figure 5C:
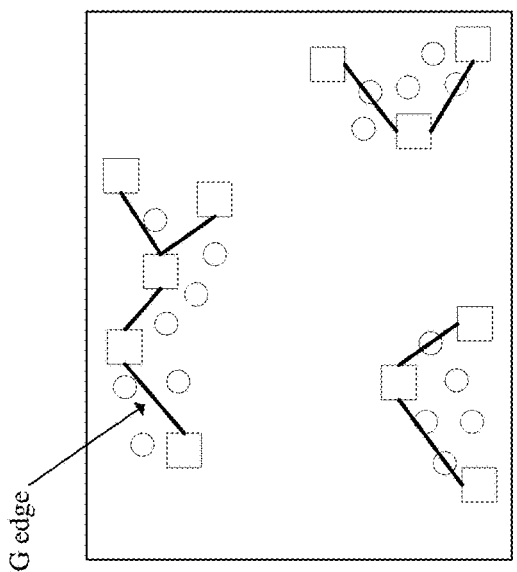
FIG. 5C illustrates an EGNG cluster moving towards a new position for continuous correct classification, if the temporal shape of the neural spikes changes during the recording.
Figure 5B:
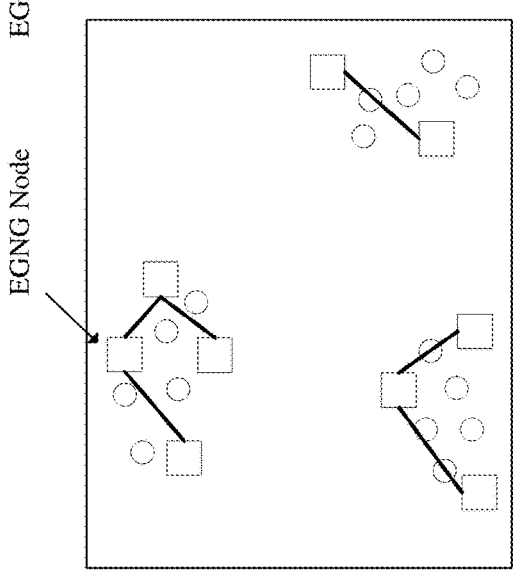
FIG. 5B illustrates a stable EGNG cluster distribution that will emerge after enough neural points are processed, allowing correct classification for subsequent incoming neural spikes.
Figure 5A:
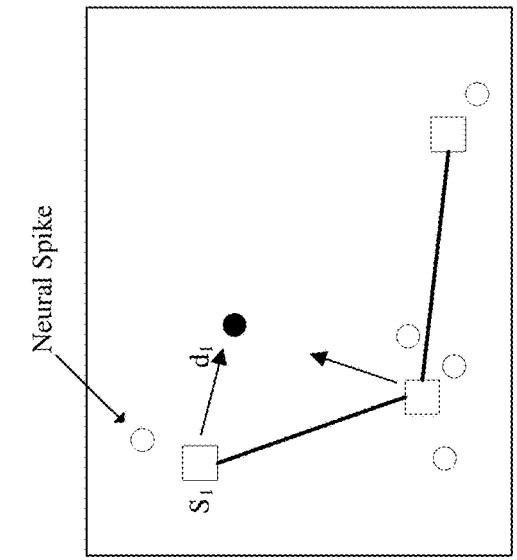
FIG. 5A illustrates the EGNG process to sort streaming neural spikes in real-time. Near the beginning of the sorting, very few neural points have been streamed in, and only a few EGNG nodes have been created. The closest EGNG node ($s_1$) and its neighing nodes are moved towards the incoming neural point.
Figure 5F:
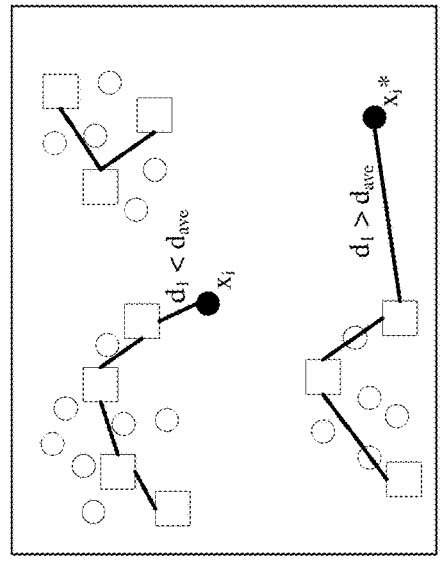
FIG. 5F illustrates how a neural point ($x_i$) is classified based on its Euclidian distance to the shortest EGNG node ($d_1$) when it is shorter than the average Euclidean distance of all EGNG points ($d_1 < d_{ave}$). In contrast, a neural point ($xi'$) having a Euclidean distance to the closest EGNG node ($d_1$) longer than the average Euclidean distance of all EGNG points ($d_1 > d_{ave}$) is classified as noise.

1) Update of the EGNG nodes based on the incoming neural spike: Unlike off-line sorting where all neural points are available, in real-time sorting, neural spikes are recorded and streamed into the process individually and sequentially. Despite this acquisition difference, the basic EGNG process of creating, deleting, and moving EGNG nodes and edges is the same in both modes. However, in real-time sorting, steps 1 to 6 of the off-line mode will be used continuously to build up the EGNG clusters, as shown in FIGS. 5A and 5B. The main difference is that instead of selecting a neural point $x_i$ from the pre-recorded data pool, the neural point $x_i$ is now the most recently streamed-in neural point.

2) Immediate classification of the incoming neural spike: Immediate classification of the neural spikes is particularly important to allow downstream data analysis to estimate brain state and respond with proper interventions. Therefore, the classification of the incoming data point is performed immediately by determining which EGNG cluster is closest to the neural point. To realize this, EGNG calculates the Euclidean distances between the new neural point $x_i$ and all the EGNG nodes $W_j$, $$d_j = \|x_i - W_j\|, j = 1 \ldots N$$

The EGNG node with the shortest distance to the new neural point $x_i$ is identified and the classification is based on identifying the EGNG cluster containing this EGNG node.

3) Movement of EGNG clusters: If the temporal shape of a neural cluster has changed over time due to probe movement or other electrophysiological drift, the closest EGNG cluster will move towards the new position, as shown in FIG. 5C. This movement is facilitated by the normal EGNG node movement towards the most recent neural points. This adaptability allows continued correct classification of the neural data, even if the temporal shape of the neural spikes has changed, which is particularly important for long-term recording.

Figure 5E:
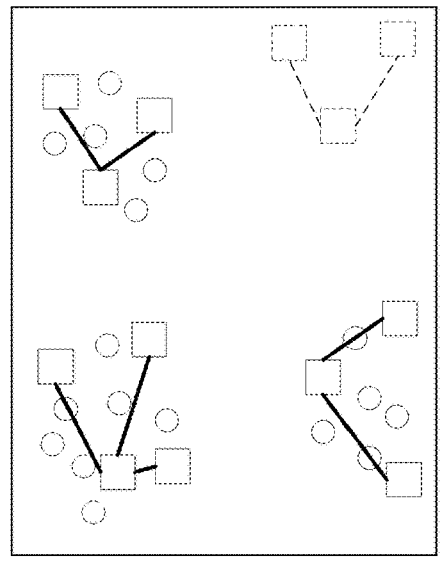
FIG. 5E illustrates an existing EGNG cluster eliminated if no neural points are coming in for the cluster group for an extended period of time.
Figure 5D:
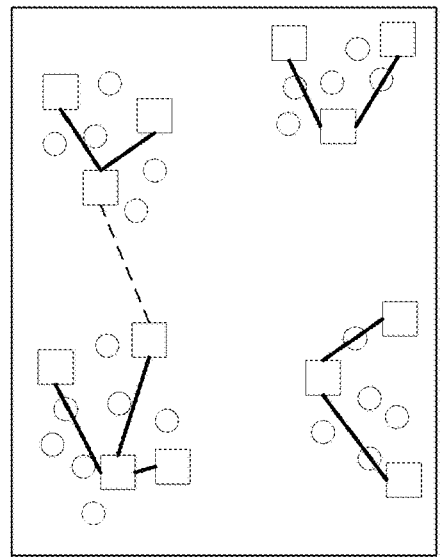
FIG. 5D illustrates a new EGNG cluster formed by the regular EGNG edge pruning process if a steady stream of neural points appears in a more distant location.

4) Deletion of obsolete EGNG clusters: Similarly, if neural spikes from a particular neuron are no longer recorded by the electrode, the corresponding EGNG cluster will be removed automatically. If the EGNG cluster no longer receives new incoming neural spikes, EGNG nodes and edges are deleted once the age parameters are matured. This removal process results in the complete deletion of the obsolete EGNG cluster, as shown in FIG. 5E.

5) Creation of new EGNG cluster and rejection of noisy signals: Neural points can appear far away from existing EGNG clusters for two reasons. The first reason is that these neural points belong to a new cluster which the electrode was not able to pick up previously. The second reason is that these neural points are actually noise signals which exceed the spike threshold and thereby enter the sorting process inappropriately. In order to differentiate between these two conditions, the shortest Euclidian distance between the neural point and the EGNG nodes are calculated, and if this distance is larger than the outlier threshold dout, this neural point is considered as an outlier. The EGNG process will further calculate the running average position xave of these outliers with $$x_{ave} \leftarrow \frac{x_i}{N_{out}} + \frac{N_{out} - 1}{N_{out}} x_{ave}$$

where $N_{out}$ is the number of recent outliers for the average. For the subsequent streaming neural points, if the Euclidian distance between the neural point and the running average xave is larger than the noise rejection threshold dn, the neural point is categorized as noise and discarded from the process. However, if the Euclidian distance of the outlier is smaller than dn, the outlier is considered as a neural point that belongs to a new neuronal recording, and the location of the neural point will be retained in the system. In addition, if the total count of these retained neural points has reached the new cluster creation threshold Nc, a new EGNG cluster will be created around these retained neural points. Once the new EGNG cluster has been created, these few retained neural points will be discarded to save system memory. Neural points belonging to this new cell subsequently streamed into the process will be correctly categorized due to the creation of the new EGNG cluster.

Pseudo-code of the on-line and real-time EGNG process to sort streaming neural spikes is listed below. This code can be run from a standard personal computer in some embodiments, or can be implemented on a FPGA or ASIC in other embodiments:

---

Process 2: Real-time EGNG implementation

---

```
For every streaming data (x_i)
  Increase the number of data by 1 (num=num+1)
  If (num<50) and (num %5==1) (initialize part of data)
    Maximum node count (N_EGNG) +=1 (for every 5 data increase the number of nodes by one)
  If (num>50) and (num %100==1)
    Maximum node count (N_EGNG) +=1 (for every 100 data increase the number of nodes by one)
  While (the number of inserted nodes < N_EGNG) and (stopflag = 1)
    For each training epoch
      Calculate the distance between existing nodes and the new datapoint
      Choose two nodes with lowest distances
        S_1 = argmin_{w_j∈N}(d_j)
        S_2 = argmin_{w_j∈N\(S_1)}(d_j)
      Set the connection of S_1 and S_2 to zero
      Update the location of S_i and its topological neighbors (S_j) using learning rates
        S_1 ← S_1 + e_{s_1}(x_i - S_1)
        S_j ← S_j + e_{nbr}(x_i - S_j)
      Update the accumulated error ("insert" parameter) of S_1 as
        insert_{s_1} ← insert_{s_1} + ||x_i - s_1||^2
      Increase the age of all edges connected to S_1
      If the number of inserted nodes > 2
        If each edge > Edge removal threshold
          Remove that edge
        If there is a node without any connection
          Remove that node and its location and insert parameters
      Decrease all error variables using Decreasing rate (β)
    If the number of inserted nodes < N_EGNG
      Determine node w_e with the largest 'insert' parameter
      Determine the node with the largest error w_e' among the connected nodes to w_e
      Insert a new node w_N between two we' and we nodes as
        w_N = 0.5(w_e + w_e')
      Remove the edge between we' and we
      Connect new node w_N to w_e' and w_e by making two edges
      Decrease insert parameters of nodes w_e' and w_e by an error rare (α)
        insert_{w_e} ← α · insert_{w_e}
        insert_{w_e'} ← α · insert_{w_e'}
      Set new node w_N insert parameter as
        insert_{w_N} ← insert_{w_e}
    To remove long edges that connected several clusters
      Calculate all EGNG edges length as
        l_{w_i,w_j} = ||w_j - w_i||
      Calculate the average of these edges' length (threshold)
        l_{ave} = mean (l_{w_i,w_j})
      For all EGNG edges length
        If l_{w_i,w_j} > l_{ave}
          Prune l_{w_i,w_j}
      Set stopflag = 0 to show that this stage of edge removing finished
    To remove low density edges
    For every edge in EGNG
      Calculate the Euclidian distances of five data points (closest to the middle of an EGNG edge) and the middle
      point location of that edge
      Calculate the average of these five distances and consider it as a label number for that edge (l_{mid}^i)
    Calculate the average of all l_{mid}^i (threshold)
        \overline{l_{mid}} = mean(l_{mid}^i)
    For every edge in EGNG
      If l_{mid}^i > \overline{l_{mid}}
        Remove the edge as it is in a very low-density area (between clusters area)
    Calculate the distance between the new data point and existing nodes
        d_j = ||x_i - w_j||, j = 1 ... N
    Find the EGNG node with the shortest distance (d_{jmin})
    If d_{jmin} < d_{out} (outlier threshold)
```

-continued

Process 2: Real-time EGNG implementation

New datapoint belongs to the cluster group containing the nearest node to datapoint
If $d_{jmin} > d_{out}$
  Put new data point in All_outliers array
  Calculate the running average position $x_{ave}$ of All_outliers array ($N_{out}$ is the length of this array)

$$x_{ave} \leftarrow \frac{x_i}{N_{out}} + \frac{N_{out} - 1}{N_{out}} x_{ave}$$

Calculate the distance between the new data point and the running average $x_{ave}$ and call it $d_{dis}$
If $d_{dis} > d_n$ ($d_n$ is the noise rejection threshold)
  New data point is categorized as noise and discarded by the process
If $d_{dis} > d_n$
    New data is considered as a member of a new cluster and keep it in a New_cluster array
    If the number of New_cluster members = $N_c$ (new cluster creation threshold)
    Consider all the members of New_cluster as a new cluster
    Insert nodes for this new cluster
    Save the positions of the new cluster's nodes and discard the data of New_cluster (New_cluster = Null)
  If the temporal shape of a cluster changed over time (a set of data ($data_{set}$) belongs to it sequentially)
    Move the nodes of that cluster ($N_{clus}$) toward that dataset ($data_{set}$)

$$N_{clus} \leftarrow N_{clus} + \frac{1}{size(N_{clus})}(data_{set} - N_{clus})$$

If a cluster is not active for couple of new streaming data
  Remove that cluster and its nodes and edges

---

Both simulated and pre-recorded electrophysiology data can be used to evaluate the performance and accuracy of the EGNG process for both the off-line and the real-time modes, as well as the FPGA hardware implementation of EGNG. The same data can also be used to compare EGNG to four other existing off-line spike sorting processes for classification accuracy and processing time.

The off-line EGNG process can be evaluated with a simulated data set containing 5 Gaussian clusters, each with 200, 150, 150, 100 and 100 neural points, respectively. Three of these Gaussian clusters are circularly distributed and the remaining two are elliptically distributed [36]. Another set of simulated data distributed as three concentric rings can be used to test whether the EGNG process can handle non-Gaussian data distributions. The three concentric rings have radii of 1.0, 2.0 and 3.0 containing 4800, 3200 and 1600 data points, respectively, with a Gaussian standard derivation of 0.14 [16]. The noisy moon data can also be used to compare the EGNG process to four other sorting processes (see below) and the data set can be generated using the make_moons function in the scikit-learn library with a total of 1,500 sample data points [37]. In order to test the on-line sorting capability of the EGNG process implemented in both software and hardware, another set of simulated data obtained from Ref. [26] can be used as streaming neural data. The data set contains 1,440,000 data points and only the first 200,000 data points were used for the elevation. The data set can also be used to evaluate the EGNG hardware implementation with an FPGA chip and the hardware sorting result can be compared to that generated by the software implementation.

FIGS. 6A-6D demonstrate the EGNG process in off-line mode when classifying simulated neural data (white circles) belonging to five different neurons. Five non-overlapping neural clusters were distributed across the vector space as shown in FIG. 6A. At the beginning of the classification, there were only three EGNG nodes (white squares) interconnected by two EGNG edges (black lines) among the neural data as in FIG. 6B. As the sorting proceeds, as shown in FIG. 6C, more EGNG nodes and edges are generated to loosely cover the entire neural distribution with EGNG nodes still interconnecting with one another. By the end of the sorting, some EGNG edges are pruned and the EGNG nodes are separated into five different EGNG clusters. At this point, the Euclidian distances from the neural points to their closest EGNG nodes are determined. The neural points are classified based on the EGNG cluster containing the closest EGNG node to the neural point. For demonstration purposes, neural points belonging to the same cluster were labeled for easy identification in FIG. 6D.

Figure 7B:
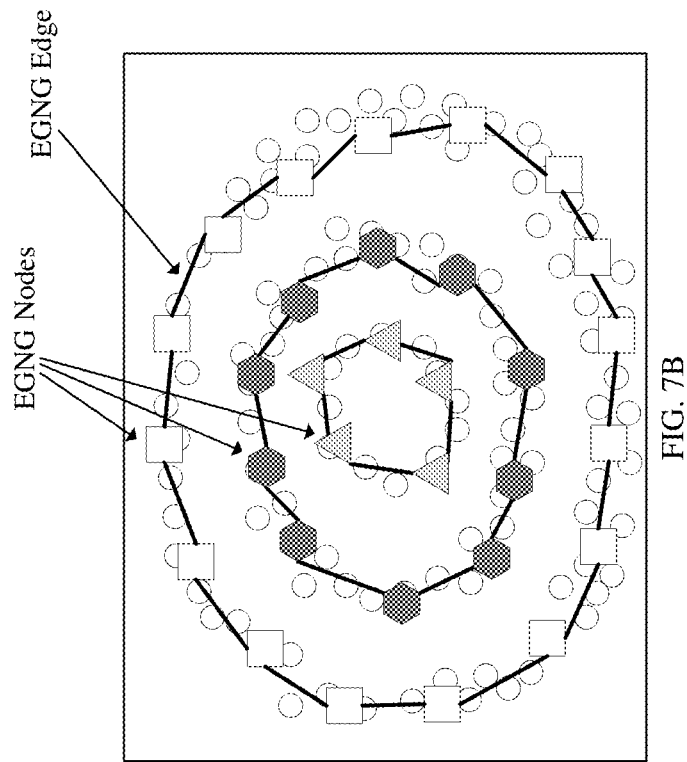
FIG. 7B illustrates the three concentric rings separated by the EGNG process. The neural points are correctly classified based on the three concentric rings.
Figure 7A:
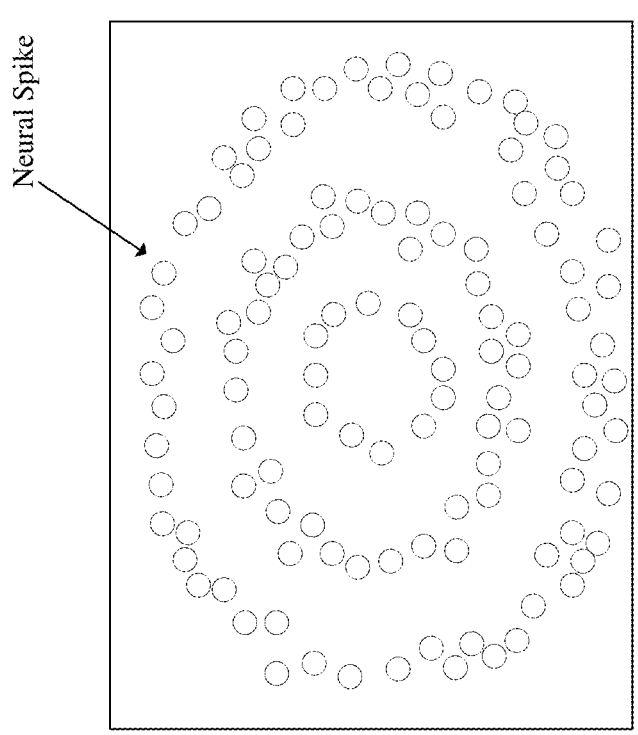
FIG. 7A is an example of how the EGNG process sorts artificial non-Gaussian distributed neural points. Three concentrically distributed neural groups were generated with radii of 3.0, 2.0, and 1.0 with a Gaussian noise standard deviation of 0.14.

The EGNG process makes no presumption about the nature of the data distribution and is robust in classifying neural clusters with non-Gaussian distributions. FIG. 7A shows synthetic neural points distributed in three concentric rings. At the beginning, EGNG nodes were randomly generated and interconnected by EGNG edges covering the three rings as one large group. After some iterations, the EGNG edges between the rings are pruned and resulted in three concentric EGNG circles. FIG. 7B shows the final classification results indicating that the neural points can successfully be classified into three separate clusters and labeled with three different colors to indicate to which EGNG cluster the points were associated.

FIG. 8A is the result of using the EGNG process to classify simulated neural points distributed in four neural clusters. Despite the four neural clusters being close to one another, there are still low-density gaps between the clusters to allow them to be separated. In order to test the capability of the EGNG process to classify closely spaced neural clusters, additional Gaussian noise with a variance of 0.16 can be added to make the neural clusters overlap closer. With the help of edge pruning at low-density areas, the EGNG process can separate the neural clusters successfully, as demonstrated in FIG. 8B.

The process can also be tested with actual neural data. All experimental procedures complied with all applicable laws and National Institutes of Health guidelines and were approved by the University of Colorado Institutional Animal Care and Use Committee (IACUC). The details of the experimental setup and the recording procedure are discussed in our previous publication and are only summarized here. In brief, the extracellular voltage trace was recorded with a high-impedance Tungsten metal electrode. The electrode was placed into the fiber tract of the fifth (trigeminal) nerve within the brain stem of an anesthetized Mongolian gerbil (Meriones unguiculatus), and the neural spikes recorded had an average signal-to-noise ratio (SNR) of 2.7. This relatively low SNR was used intentionally to test the sorting capabilities of the process. Individual neural spikes were isolated from the recorded trace through setting a threshold 2 times above the noise average and subsequently converted to feature vectors using PCA before sending to the EGNG process for sorting.

Figure 9D:
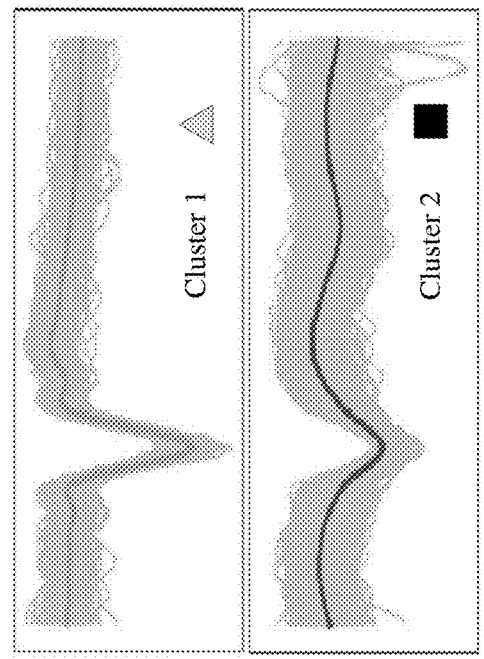
FIG. 9D illustrates the temporal waveforms and the waveform averages of the two separated clusters.
Figure 9C:
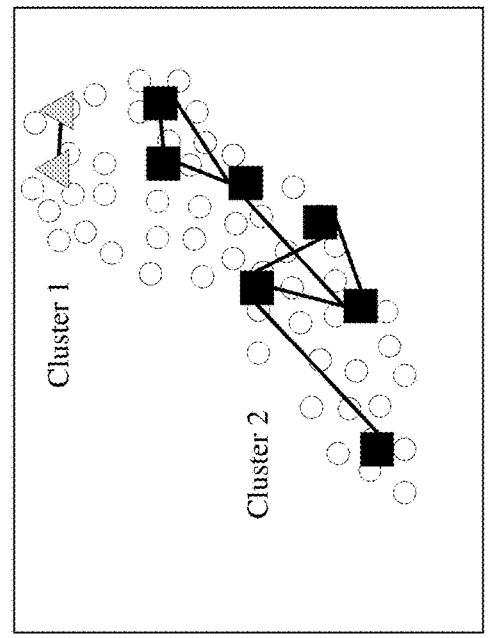
FIG. 9C illustrates that the EGNG edge between the two neural groups was pruned to correctly separate the neural spikes into two EGNG clusters.
Figure 9A:
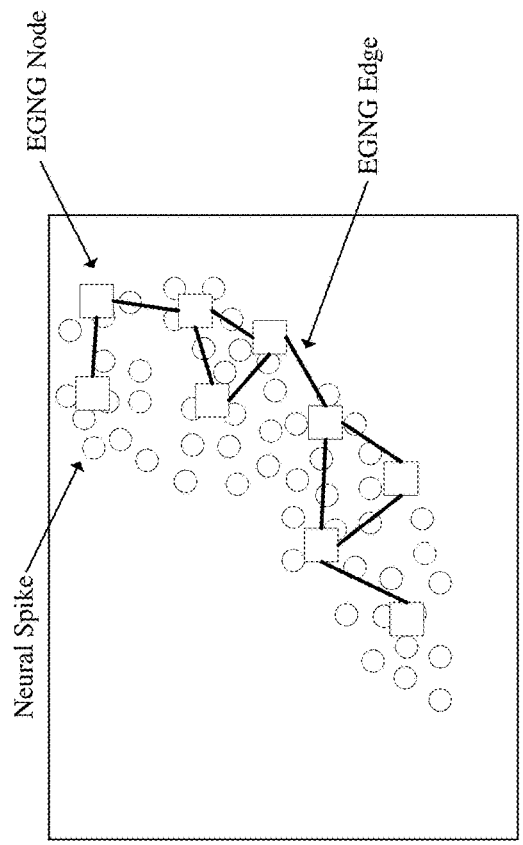
FIG. 9A is an example demonstrating how the EGNG process can sort pre-recorded real neural spikes. At the beginning of the sort, EGNG nodes were connected together as a single large EGNG group.
Figure 9B:
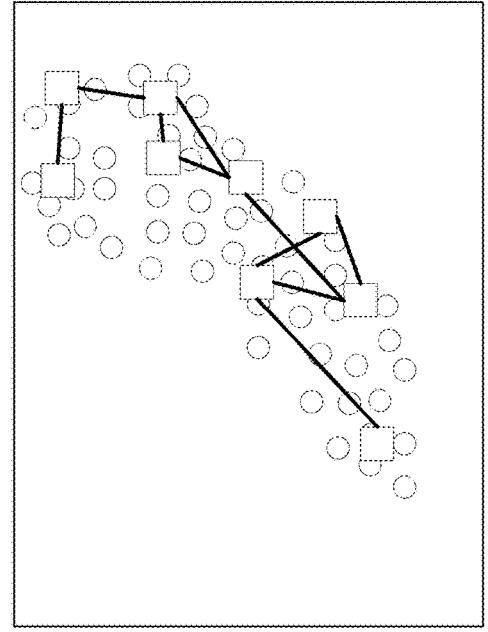
FIG. 9B illustrates that the EGNG nodes were pulled towards the areas with higher concentrations of neural spikes.
Figure 10B:
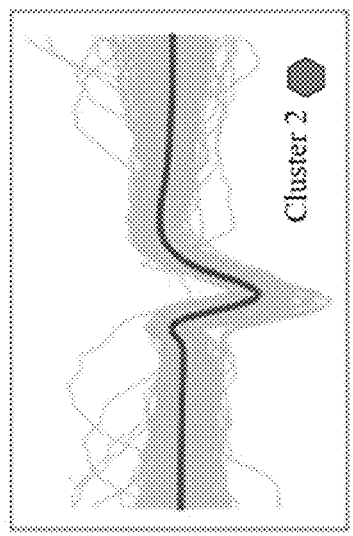
FIG. 10B illustrates the temporal waveforms and the waveform averages of the first separated cluster for hc–1.
Figure 10C:
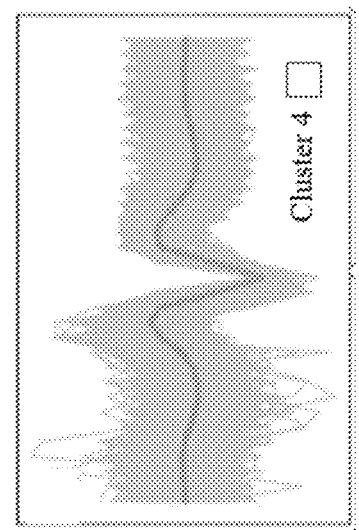
FIG. 10C illustrates the temporal waveforms and the waveform averages of the second separated cluster for hc–1.
Figure 10E:
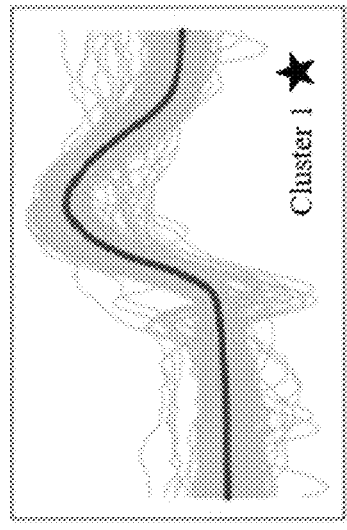
FIG. 10E illustrates the temporal waveforms and the waveform averages of the first separated cluster for NCHybrid136.
Figure 10F:
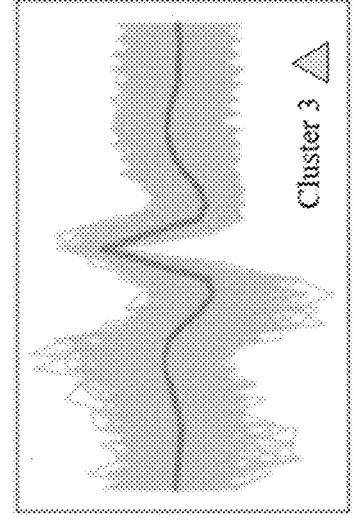
FIG. 10F illustrates the temporal waveforms and the waveform averages of the second separated cluster for NCHybrid136.
Figure 10A:
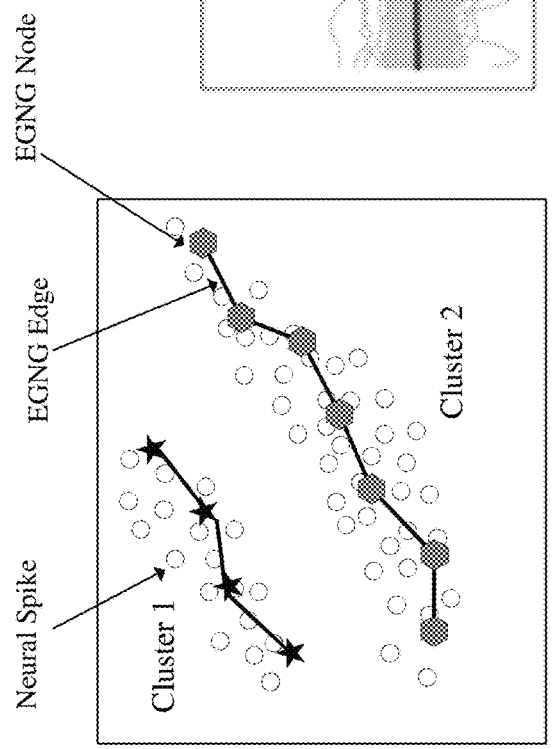
FIG. 10A is an example of how the EGNG process can be used to classify a publicly available set of neural data (hc–1)
Figure 10D:
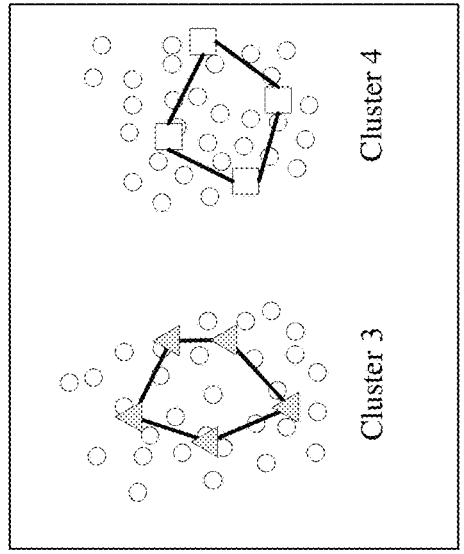
FIG. 10D is an example of using the EGNG process to classify a different publicly available set of neural data (NCHybrid136)

Pre-recorded neural spikes measured from the fifth nerve of an anesthetized gerbil can be used to demonstrate the sorting capability of the EGNG process for real neural data. The temporal shapes of the recorded neural spikes have similar structures such as a prominent negative peak, making the ground truth determination of the classification difficult, and the classification accuracy therefore cannot be calculated. The EGNG process, however, determined that there were two separable clusters, with one cluster having larger negative peaks than those of the other cluster, as shown in FIG. 9D. At the beginning of the sort, EGNG nodes were all connected together forming a large EGNG cluster covering the entire neural data, as shown in both FIG. 9A and FIG. 9B. In this example, the EGNG process, however, took advantage of the fact that the density of neural points was more concentrated in the cluster centers than the perimeters, and the EGNG nodes were then separated at the boundary and finally broken into two disconnected clusters, as shown in FIG. 9C. It is worth mentioning that the lower cluster fired about twice as often compared to the upper cluster. Also, neural spikes of the lower cluster had much worse signal-to-noise ratio than those of the upper clusters. Given their similar temporal structures, these two groups of neural spikes are difficult to sorted, but EGNG handles them well and is able to separate them into two closely packed clusters.

Two publicly available neural data sets can be used to further evaluate the classification capability of the off-line EGNG process. The first data set (hc-1, animal: 166, file: d16613.001.dat) was recorded from the CA1 hippocampal region and was developed as a benchmark for spike detection and sorting. The neural spikes were isolated by a threshold of 2 times above the noise level, and were converted to neural points in the vector space using PCA, followed by EGNG classification. The second data set (NCHybrid136) was constructed from two neural datasets of a 32-channel probe in the rat cortex. Since the second data set contains 32 channels, channel 3 was randomly chosen for the analysis. The recording was initially processed by a $5^{th}$-order Butterworth high-pass filter with a cut-off frequency of 200 Hz to remove the low-frequency local field potential component, followed by a threshold of 2 times above the noise average to isolate the neural spikes. A total of 1902 neural spikes were isolated from the first 500,000 data points of the recording and was converted to the vector space into neural points using PCA for EGNG classification.

FIGS. 10A-10F show the results of the EGNG classification results for both the hc-1 and NCHybrid136 data sets, and both of the data sets resulted in two EGNG clusters respectively. The corresponding temporal waveforms and the calculated waveform averages of the clusters are also plotted in FIGS. 10B and 10C for the hc-1 data set, and in FIGS. 10E and 10F for the NCHybrid136 data set. The waveform averages show distinctive differences between the different clusters of neural spikes.

Figure 11B:
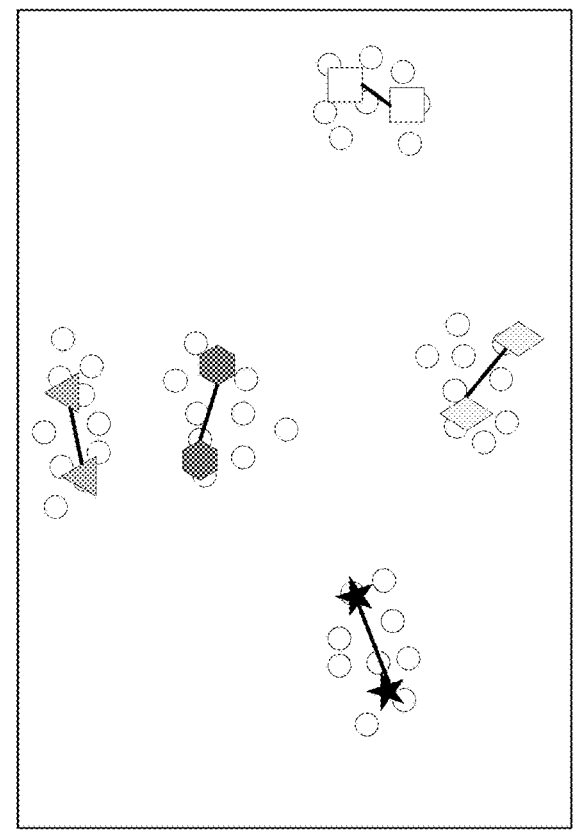
FIG. 11B illustrates that the remaining 500 neural points of the split dataset can be classified correctly using the learned EGNG clusters from 8A.
Figure 11A:
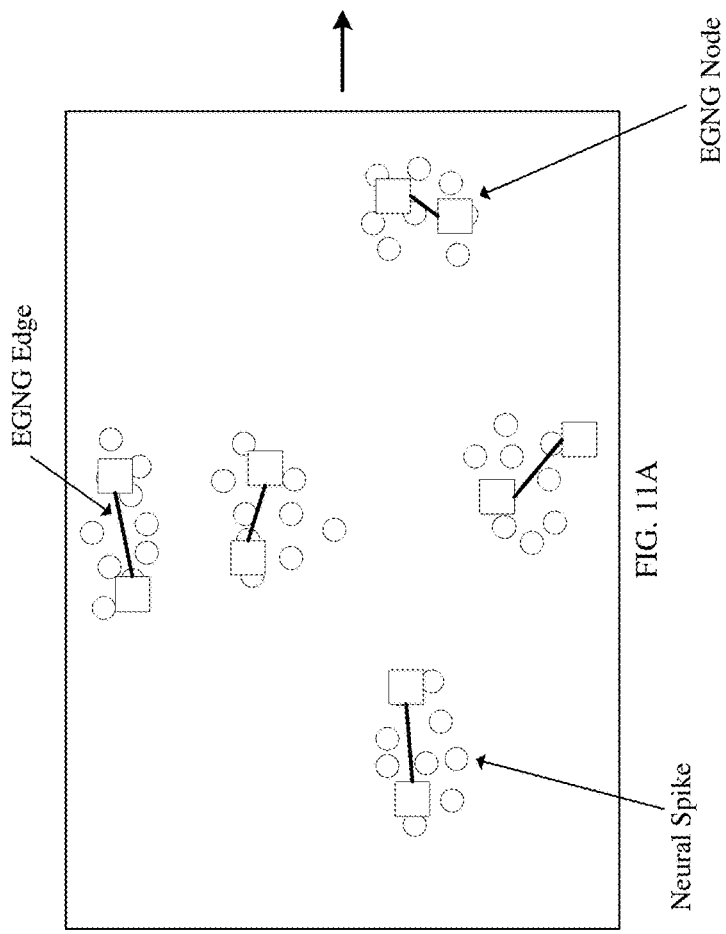
FIG. 11A illustrates an example of neural spike sorting off-line with the EGNG process. In this case, the EGNG clusters can be trained by the first 200 neural points of a split dataset.

FIGS. 11A-11B demonstrate the EGNG clusters can be separately trained and evaluated using a split dataset. The entire dataset contains 700 neural points and the first 200 neural points can be used to train the EGNG nodes in the off-line mode to reach convergence and the EGNG nodes were separate into five different clusters. After the training, the remaining 500 data points can be classified using the EGNG clusters based on the minimum Euclidian distances to the EGNG nodes.

Figure 12:
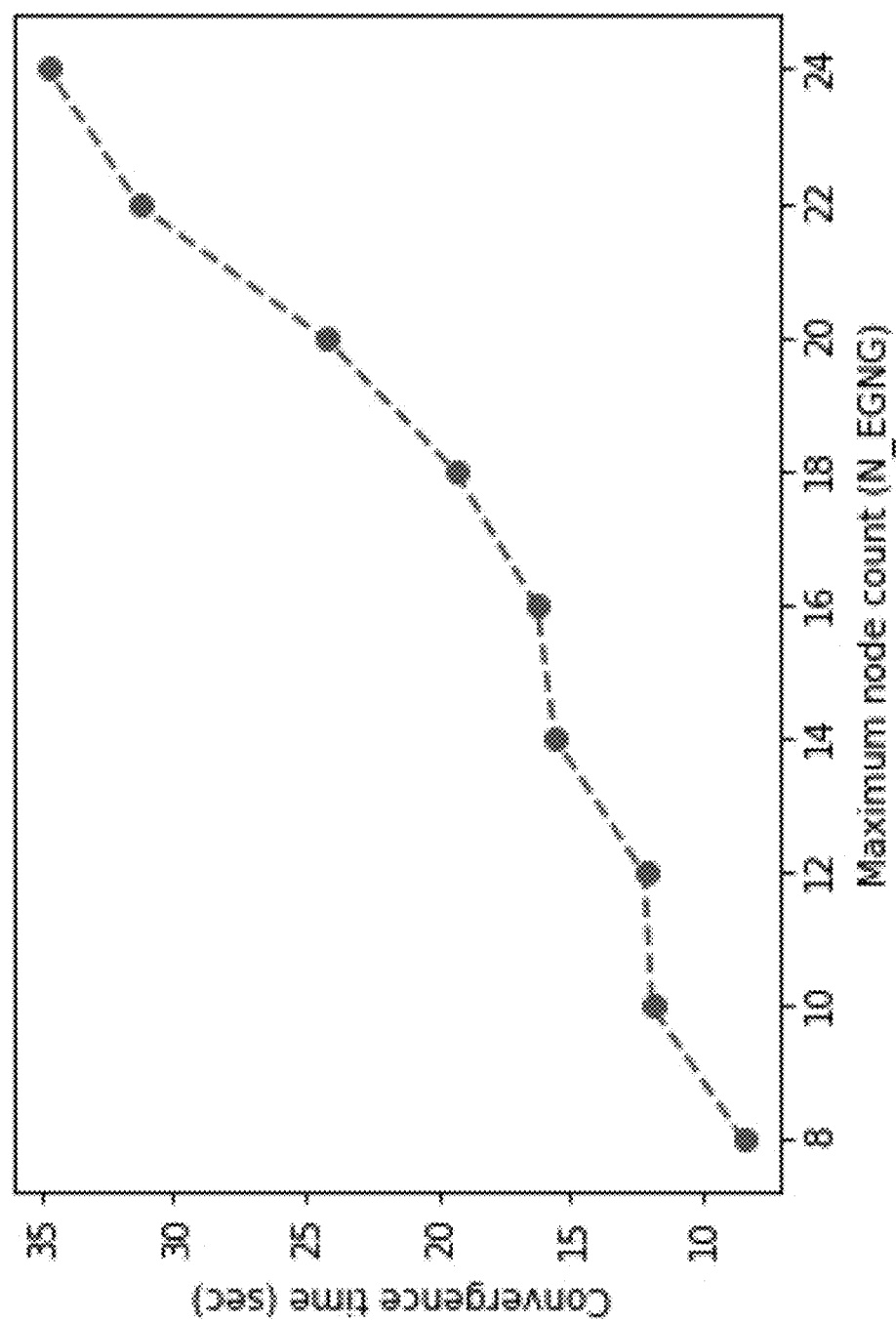
FIG. 12 illustrates the convergence time of the off-line EGNG process plotted against an increased number of EGNG nodes.

The convergence time of the off-line EGNG process against an increased number of EGNG nodes is plotted in FIG. 12, and the convergence time follows a linear trend as the EGNG nodes increases. The convergence time can be measured on a 16 GB, 3.4 GHz Intel i7 computer running the EGNG process.

The EGNG process in off-line mode was compared to four other off-line sorting techniques—Density-Based Spatial sorting of Applications with Noise (DBSCAN), K-means, EM, and SPC—to evaluate the performance of these processes compared to EGNG. DBSCAN considers data points with close Euclidian distances as neighbors and assigns these neighbors as a group if the local density is higher than a threshold. Otherwise, the neighbors are considered as outliers. K-mean assumes neural clusters are Gaussian distributed with a known total number of clusters, and moves the centers of these Gaussian clusters towards the centers of the neural points in order to best cover them. EM is one of the so-called "soft sorting methods" which applies two steps—the expectation (E) step and the maximization (M) step—iteratively to maximize the Posteriori (MAP) or Maximum Likelihood (ML) estimates for the Gaussian clusters to best cover the neural distribution. Custom python code can be written for DBSCAN, K-means and EM using the built-in functions of the scikit-learn library and the software package Wave_Clus was used for SPC classification. The aforementioned simulated data sets can be fed into the processes for a comparison of results with off-line EGNG.

In this implementation, the EGNG process can be compared to four other commonly used sorting processes (DBSCAN, K-means, EM and SPC) for sorting accuracy. The sorted results are displayed in FIGS. 13A-13T. Four datasets (noisy moon data, 5 simulated clusters, three anisotropic Gaussian clusters, pre-recorded real neural spikes from a gerbil) can be submitted to the four process (the above three and EGNG) for comparison. The true positive (tp), the false negative (fn) and the false positive (fp) can be calculated based on the sorted results to obtain the F1-scores for the four sorting processes for quantitative comparison. The F1-score is defined as $$F_1 = 2 \times \left( \frac{\text{precision} \times \text{recall}}{\text{precision} + \text{recall}} \right)$$

where $$\text{precision} = \frac{tp}{tp + fp}$$

$$\text{recall} = \frac{tp}{tp + fn}$$

The F1-score has a value between 0 and 1 in which 1 indicates a 100% correctness for the sort. The means and the standard derivations of the F1-scores evaluated from 10 repeated runs for the four sorting methods are listed in Table 2. The results indicate that the EGNG process can sort correctly for all the four datasets with high F1-scores, while the other four processes have problems sorting at least one of the data sets. This is largely due to the fact that the EGNG process can handle closely spaced and non-Gaussian clusters. The convergence time of the EGNG process can also be compared to the other four sorting processes using the 5 simulated clusters dataset on a 16 GB, 3.4 HHz Intel i7 computer. Due to the process simplicity of EGNG, EGNG has the shortest convergence time among the five processes, as shown in Table 3. Moreover, the EGNG was written in the Python programming language. Python is an interpreting computer language that is notoriously slow in handling for and while loops. By contrast, the other processes were highly optimized with C language in the Scikit-learn library. Thus, EGNG will converge even faster than indicated in table 3, if properly optimized.

TABLE 2

Means and standard deviations of F1-scores comparing the five sorting processes in which EGNG process has the highest F1-score among the four datasets.

|  | Data 1 (moon data) | Data 2 (5-clusters) | Data 3 (Anisotropic) | Data 4 (real data) |
| --- | --- | --- | --- | --- |
| DBNSCAN | $1.0 \pm 0$ | $0.923 \pm 3.53 \times 10^{-8}$ | $0.996 \pm 3.18 \times 10^{-8}$ | $0.227 \pm 5.49 \times 10^{-9}$ |
| EM | $0.855 \pm 1.36 \times 10^{-6}$ | $0.766 \pm 2.62 \times 10^{-8}$ | $1.0 \pm 0$ | $0.720 \pm 2.80 \times 10^{-5}$ |
| K-means | $0.754 \pm 4.88 \times 10^{-6}$ | $0.604 \pm 2.34 \times 10^{-8}$ | $0.827 \pm 2.73 \times 10^{-8}$ | $0.812 \pm 2.12 \times 10^{-6}$ |
| DBNSCAN | $1.0 \pm 0$ | $0.923 \pm 3.53 \times 10 - 8$ | $0.996 \pm 3.18 \times 10 - 8$ | $0.227 \pm 5.49 \times 10 - 9$ |
| EM | $0.855 \pm 1.36 \times 10 - 6$ | $0.766 \pm 2.62 \times 10 - 8$ | $1.0 \pm 0$ | $0.720 \pm 2.80 \times 10 - 5$ |
| K-means | $0.754 \pm 4.88 \times 10 - 6$ | $0.604 \pm 2.34 \times 10 - 8$ | $0.827 \pm 2.73 \times 10 - 8$ | $0.812 \pm 2.12 \times 10 - 6$ |

TABLE 3

Convergence time in seconds comparing EGNG to the four other sorting processes in classifying data 2 (5-clusters). Even unoptimized, EGNG has the shortest convergence time.

|  | Convergence time (sec) of Data 2 (5-clusters) |
| --- | --- |
| DBNSCAN | 6.013 |
| EM | 5.621 |
| K-means | 8.351 |
| SPC | 6.241 |
| EGNG | 5.408 |

The convergence time and sorting accuracy can also be evaluated as the dimensions of the EGNG nodes and the neural data were increased. The benchmarks can be calculated on the same i7 computer using the same data set of FIG. 8A. As shown in Table 4, the convergence time is approximately increased by a factor of 2 as the EGNG node and data dimensions are increased from 2 to 5. In addition, the sorting accuracy is unchanged as the dimension is increased.

TABLE 4

Changes of the convergence time and the sorting accuracy off-line as the dimension of the EGNG nodes and the neural data were increased from 2 to 5.

| EGNG node dimension | Convergence time (sec) | Sorting accuracy |
| --- | --- | --- |
| 2 | 10.88 | 0.971 |
| 3 | 17.6 | 0.968 |
| 4 | 20.8 | 0.974 |
| 5 | 23.97 | 0.973 |

The true power of the EGNG process rests on its ability to rapidly and adaptively classify streaming neural spikes in real-time. FIGS. 14A-14F show the process of how EGNG clusters are developing through analyzing streaming neural spikes in real-time. At the beginning of the sorting, as shown in FIG. 14A, only a few initial neural points entered the process and a few EGNG nodes are created interconnected as one EGNG cluster to cover them. Since the full distribution of the neural points has not been learned by the EGNG nodes at this early stage, these early neural points are classified to belong to a first EGNG cluster. As more neural points are streamed into the process, more EGNG nodes are created and separated into EGNG clusters covering each of the neural clusters better, based on the EGNG sorting process. Incoming neural points are then classified based on the EGNG cluster distribution at the time, as shown in FIGS. 14B to 14D. As more and more neural points are streamed into the sorting process and analyzed, the full neural distribution is then learned by the EGNG nodes, and the EGNG clusters becomes stable. Subsequently, incoming neural points are classified correctly, as shown in FIGS. 14E and 14F. In these figures, colors are used to represent the assigned cluster of the neural point at the time the point is analyzed. It is noted that some early neural points were not correctly classified at the beginning of the sorting, because the neural distribution had not yet been fully learned, and the process had to rely on only a few neural points to build the neural distribution, resulting in some early classification errors. As more neural points stream in, the full neural distribution is more thoroughly learned by the EGNG clusters, and the subsequent classification is correct. This learning period is brief and only requires the first tens of neural spikes, as demonstrated in FIGS. 14A-14F. This initial error will not pose a significant problem for data analysis in a real-time closed-loop setting, especially during longer recording periods. Note that these initial neural points were intentionally not reanalyzed to allow rapid classification for immediate downstream data analysis.

In addition to the ability to learn the neural distribution rapidly in real-time, another major advantage of EGNG is its flexibility to adapt to neural distribution changes for continued and correct neural sorting, as well as the ability to differentiate actual neural spikes from noise. FIG. 15A shows that the EGNG process has initially learned the neural distribution and correctly covers it with three EGNG clusters. FIG. 15B shows how new neural points can be streamed into the left side of the third cluster (light grey) located at the lower part of the figure. These new neural points represent a situation as it might occur during long-term electrophysiological recordings when the implanted electrode moves slightly, resulting in a temporal shape change of the neural spikes and a location shift for the neural points in the vector space. As more neural points are streamed into the left of the cluster, the EGNG nodes of the cluster are shifted towards these new neural points to the left, as displayed in FIG. 15C. The movements of EGNG clusters allow the neural points to be continuously and correctly classified, even when the physiological conditions are altered or drift.

Electrode movement or physiological drift can also result in picking up additional neural spikes from a neuron that was previously too far away from the electrode to yield a useful signal. In this situation, EGNG can dynamically create new EGNG clusters to add to the existing EGNG clusters for correct sorting. FIG. 15D shows three stable EGNG clusters covering the neural distribution. Next, additional neural points are streamed in at a location away from the existing clusters (top right), as shown in FIG. 15E. These remote neural points cause the process to generate new EGNG nodes and move towards them. In this manner, a new EGNG cluster can be created and neural points at the vicinity were classified as belonging to the new cluster, as shown in FIG. 15F.

Finally, electrode movement might result in the loss of neural spikes from a neuron. In this case, the EGNG cluster covering these neural spikes should be removed. FIGS. 15G-15I demonstrate this situation by only streaming in neural points belonging to two EGNG clusters, leaving the third cluster (lower right) without new neural points to strengthen it. As a result, the third EGNG cluster without neural spikes is removed from the distribution, leaving only the first two EGNG clusters to continue for the classification.

EGNG can easily integrate with noise rejection to separate unwanted noisy spikes from genuine neural spikes. Neural spikes from the same neuron tend to cluster close to one another, but noisy spikes are scattered and not close to these clusters. If the Euclidian distance of a point to its nearest EGNG node is longer than the noise rejection threshold ($d_n$), the point is rejected as noise and is not classified. In FIG. 15K, all new points are colored in grey; the points closer to a cluster are colored with the respective clusters and the points that are classified as noise are colored in dark gray and rejected.

In some embodiments, the EGNG process can be implemented using digital electronic hardware. A hardware implementation of the EGNG process can be developed for an FPGA chip to demonstrate the real-time spike sorting capability of EGNG. An FPGA development broad (Arty A7-35T, Xilinx, CA) containing an FPGA chip (xc7a35ticsg324-1L, Xilinx, CA) running on a 20 MHz system clock can be used for the implementation. The EGNG code for the FPGA hardware was written using Verilog, which is a hardware description language, and was compiled and implemented on the FPGA using the Vivado design suite (Xilinx, CA).

Figure 16B:
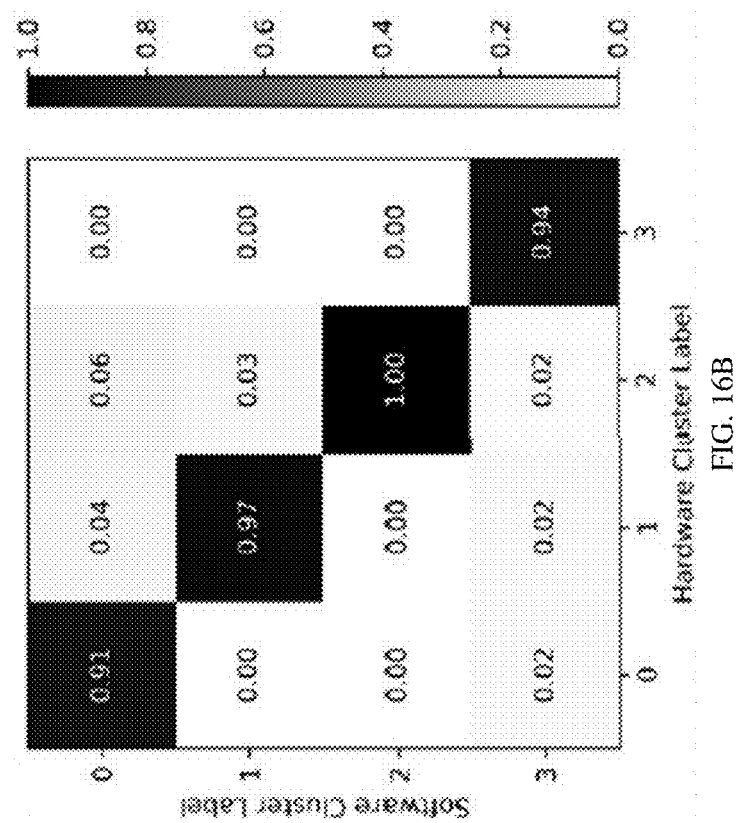
FIG. 16B is the normalized confusion matrix comparing the classification results between the software and hardware EGNG.
Figure 16A:
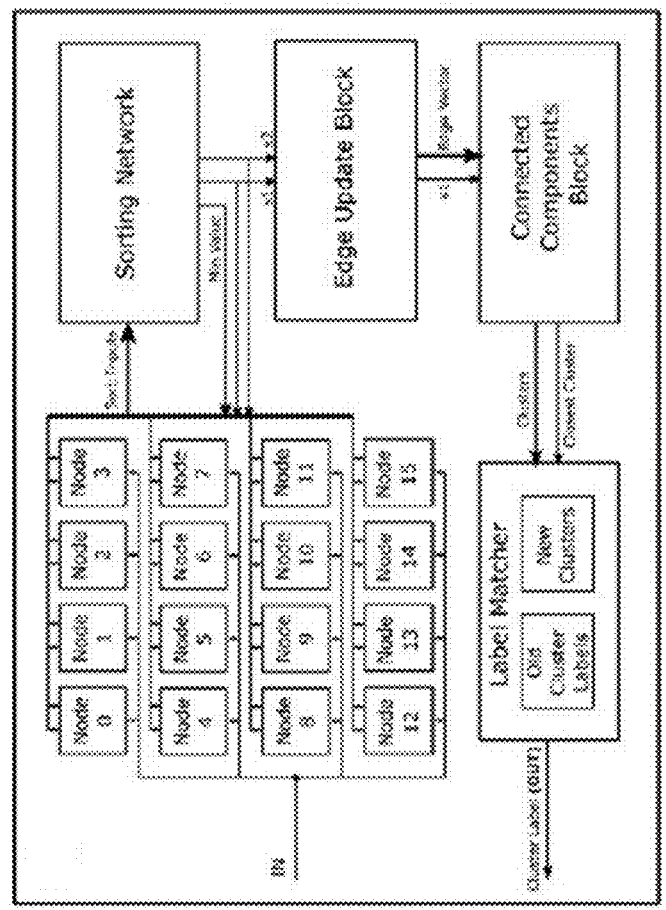
FIG. 16A is an embodiment of implementing the EGNG process on an FPGA to demonstrate hardware real-time neural spike classification capability. In this embodiment, sixteen EGNG nodes are implemented to simultaneously compute the Euclidian distances between the input neural spike data (IN) and each of the EGNG nodes. A sorting network was built to determine $S_1$ and $S_2$ nodes. An edge update block was built to update EGNG edges creation and pruning, and a connected components block was built to find clusters of connected EGNG nodes. A label matcher block was used to maintain consistency between clusters and cluster labels. Finally, the neural spike data was classified for the output.

FIG. 16A illustrates the overall design of the EGNG hardware implementation. The FPGA design was separated into several hardware blocks: (1) 16 interconnected EGNG nodes, (2) a sorting network block, (3) an edge update block, (4) a connected component block, and (5) a label matcher block. As a neural spike is streamed into the FPGA, the position of the neural spike in the vector space is sent to all EGNG nodes simultaneously, and the Euclidian distances between the neural spikes to all the EGNG nodes is calculated in parallel with a single clock cycle. Based on the calculated Euclidian distances, the sorting network block then determines the closest two EGNG nodes ($S_1$ and $S_2$), which are then used to update the positions and insert parameters of all the EGNG nodes. If the number of iterations exceeds the value of $\lambda$, the sorting step is repeated with the insert parameters of the EGNG node, and a new EGNG node is inserted. The edge update block then creates new EGNG edges and deletes old ones, and condenses all EGNG edges into a single vector representing a triangular matrix from which connected components can be determined. The edge vector is passed into the connected components block, which then determines the clusters of EGNG nodes connected by EGNG edges. The resulting clusters are sent to the label matcher block that compares the most recently identified clusters to the previous set of labeled clusters in order to ensure that cluster labels for each group of connected EGNG nodes remain consistent. Finally, the input neural spike is classified according to the EGNG cluster containing the $S_1$ node, and a cluster label is assigned to the neural spike at the output.

FIGS. 16C-16H show snapshots of the EGNG sorting with the FPGA hardware using the same artificial data set used to generate FIGS. 14A-14F in software sorting as inputs. The hardware EGNG sorting follows the same evolution as that in the software classification to separate and form EGNG clusters, and finally results in four well-separated EGNG clusters, demonstrating the same sorting capability in both hardware and software. FIG. 16I compares the results of the hardware and software EGNG sorting and shows identical sorting number assignments, except in the early start of the process when the four clusters were not yet formed in the hardware implementation. A normalized confusion matrix is also constructed to demonstrate the sorting agreement between the hardware and software implementation, as shown in FIG. 16B. Agreement values between 0.91 to 1.00 are obtained, and the agreements can further be improved by using more neural spikes as the disagreements mainly occurred in the beginning of the sorting.

The worst-case sorting latency between the time when the neural spike is sent to the FPGA and when the sorting label assignment is determined, is 3.10 µs (62 clock cycles), allowing a minimum of 322,580 neural spikes to be clustered per second. However, several of the FPGA modules were not optimized and future improvements can be made to further reduce the sorting latency and increase the number of neural spikes that can be handled by the FPGA hardware.

In some embodiments, the EGNG process can be implemented to sort neural spikes recorded form an electrode with multiple recording sites. Multiple recording sites spike sorting can be realized by adding an additional dimension in the vector space to represent the recording site number. In this manner, neural points recorded from different recording sites are presented in their respective planes, and EGNG nodes and edges can cover these planes to classify the neural spikes accordingly.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A method of operating Enhanced Growing Neural Gas (EGNG) circuitry to associate neuronal spikes with cellular neurons, the EGNG circuitry comprising:
   sensor circuitry comprising a recording electrode which detects neuronal signals generated by the cellular neurons;
   processing circuitry comprising a peak isolation module and an EGNG module, wherein the peak isolation module receives the neuronal signals from the sensor circuitry and isolates neuronal spikes from the neuronal signals; and
   the method comprising, by the EGNG module:
   receiving, from the peak isolation module, the neuronal spikes;
   generating a distribution of EGNG nodes in vector space;
   training EGNG clusters to approximate the neuronal spikes, wherein each of the EGNG clusters comprises a set of EGNG nodes connected by EGNG edges, and wherein training the EGNG clusters comprises, for each neuronal spike of the neuronal spikes:
      assigning the neuronal spike to a point in the vector space;
      identifying a set of closest ones of the EGNG nodes to the neuronal spike;
      connecting the set of closest ones of the EGNG nodes with one or more EGNG edges;
      modifying the set of the closest ones of the EGNG nodes to reduce the distances between the neuronal spike and the set of the closest ones of the EGNG nodes;
      adding a new EGNG node to the vector space when according to a distance parameter and deleting unconnected EGNG nodes;
      adding one or more new EGNG edges between the new EGNG node and the set of closest ones of the EGNG nodes and deleting EGNG edges exceeding a distance threshold; and
      associating the neuronal spike with an EGNG cluster; and
   associating an EGNG cluster of the EGNG clusters with a cellular neuron of the cellular neurons; and
   transferring output data that indicates the cellular neuron of a neuronal spike based on the associated EGNG cluster of the cellular neuron.

2. The method of claim 1 wherein the processing circuitry generating the distribution of the EGNG nodes in the vector space comprises assigning the EGNG nodes to random points in the vector space.

3. The method of claim 1 wherein the processing circuitry assigning the neuronal spike to the point in the vector space comprises selecting the point based on a spike waveform in the neuron signal that corresponds to a proximity of the cellular neuron to the sensor circuitry.

4. The method of claim 1 further comprising the processing circuitry determining an age of one of the one or more new EGNG edges and deleting the one of the one or more new EGNG edges based on the age.

5. The method of claim 1, wherein associating the EGNG cluster with the cellular neuron comprises associating the EGNG cluster with the cellular neuron based on the one or more new EGNG edges when a quantity of the EGNG nodes and the new EGNG nodes exceeds a node threshold.

6. The method of claim 1 wherein the processing circuitry receiving the neuronal signal and transferring the output data that indicates the cellular neuron in association with the neuronal spike comprises receiving and processing the neuronal signal in real-time to transfer the output data in real-time without off-line storage and processing of the neuronal signal.

7. The method of claim 1 wherein the recording electrode is located in a brain of a human or animal.

8. A system for operating Enhanced Growing Neural Gas (EGNG) circuitry to associate neuronal spikes with cellular neurons, the system comprising:
   sensor circuitry comprising a recording electrode which detects neuronal signals generated by the cellular neurons;
   processing circuitry comprising a peak isolation module and an EGNG module, wherein the peak isolation module receives the neuronal signals from the sensor circuitry and isolates neuronal spikes from the neuronal signals, wherein the processing circuitry comprises one of: a Field Programmable Gate Array and an Application-Specific Integrated Circuit, and wherein the EGNG module is configured to:
   train EGNG clusters to approximate the neuronal spikes, wherein each of the EGNG clusters comprises a set of EGNG nodes connected by EGNG edges, and wherein to train the EGNG clusters the processing circuitry is configured to, for each neuronal spike of the neuronal spikes:
      generate a distribution of EGNG nodes in vector space;
      assign the neuronal spike to a point in the vector space;
      identify a set of closest ones of the EGNG nodes to the neuronal spike;
      connect the set of closest ones of the EGNG nodes with one or more EGNG edges;
      modify the set of the closest ones of the EGNG nodes to reduce the distances between the neuronal spike and the set of the closest ones of the EGNG nodes;
      add a new EGNG node to the vector space when according to a distance parameter and delete unconnected EGNG nodes;
      add one or more new EGNG edges between the new EGNG node and the set of closest ones of the EGNG nodes and delete EGNG edges exceeding a distance threshold; and
      associate the neuronal spike with an EGNG cluster; and
   associate an EGNG cluster of the EGNG clusters with a cellular neuron of the cellular neurons; and
   transfer output data that indicates the cellular neuron in association with the neuronal spike.

9. The system of claim 8 wherein to generate the distribution of the EGNG nodes in the vector space the EGNG module assigns the EGNG nodes to random points in the vector space.

10. The system of claim 8 wherein to assign the neuronal spike to the point in the vector space, the EGNG module is configured to select the point based on a spike waveform in the neuronal signal that corresponds to a proximity of the cellular neuron to the sensor circuitry.

11. The system of claim 8 wherein the EGNG module is further configured to determine an age of one of the one or more new EGNG edges and delete the one of the one or more new EGNG edges based on the age.

12. The system of claim 8 wherein to associate the EGNG cluster with the cellular neuron, the EGNG module is configured to associate the EGNG cluster with the cellular neuron based on the one or more new EGNG edges when a quantity of the EGNG nodes and the new EGNG nodes exceeds a node threshold.

13. The system of claim 8 wherein to receive the neuronal signal and to transfer the output data that indicates the cellular neuron in association with the neuronal spike, the processing circuitry is configured to receive and process the neuronal signal in real-time to transfer the output data in real-time without off-line storage and processing of the neuronal signal.

14. The system of claim 8 wherein the recording electrode is located in a brain of a human or animal.

15. One or more non-transitory computer-readable storage media having program instructions stored thereon that, when executed by one or more processors operatively coupled with the one or more non-transitory computer-readable storage media, direct a computing apparatus to at least:
   receive, from a recording electrode, neuronal signals generated by cellular neurons;
   isolate neuronal spikes from the neuronal signals;
   train EGNG clusters to approximate the neuronal spikes, wherein each of the EGNG clusters comprises a set of EGNG nodes connected by EGNG edges, and wherein to train the EGNG clusters the computing apparatus is configured to, for each neuronal spike of the neuronal spikes:
      generate a distribution of EGNG nodes in vector space;
      assign the neuronal spike to a point in the vector space;
      identify a set of closest ones of the EGNG nodes to the neuronal spike;
      connect the set of closest ones of the EGNG nodes with one or more EGNG edges;
      modify the set of the closest ones of the EGNG nodes to reduce the distances between the neuronal spike and the set of the closest ones of the EGNG nodes;
      add a new EGNG node to the vector space when according to a distance parameter and delete unconnected EGNG nodes;
      add one or more new EGNG edges between the new EGNG node and the set of closest ones of the EGNG nodes and delete EGNG edges exceeding a distance threshold; and
      associate the neuronal spike with an EGNG cluster; and
   associate an EGNG cluster of the EGNG clusters with a cellular neuron of the cellular neurons; and
   transfer output data that indicates the cellular neuron in association with the neuronal spike.

16. The one or more non-transitory computer-readable storage media of claim 15, wherein to generate the distribution of the EGNG nodes in the vector space, the program instructions direct the computing apparatus to assign the EGNG nodes to random points in the vector space.

17. The one or more non-transitory computer-readable storage media of claim 15, wherein to assign the neuronal spike to the point in the vector space, the program instructions direct the computing apparatus to select the point based on a spike waveform in the neuronal signal that corresponds to a proximity of the cellular neuron to the sensor circuitry.

18. The one or more non-transitory computer-readable storage media of claim 15, wherein the program instructions further direct the computing apparatus to determine an age of one of the one or more new EGNG edges and delete the one of the one or more new EGNG edges based on the age.

19. The one or more non-transitory computer-readable storage media of claim 15, wherein to associate EGNG cluster with the cellular neuron, the program instructions direct the computing apparatus to associate the EGNG cluster with the cellular neuron based on the one or more new EGNG edges when a quantity of the EGNG nodes and the new EGNG nodes exceeds a node threshold.

20. The one or more non-transitory computer-readable storage media of claim 15, wherein to receive the neuronal signal and to transfer the output data that indicates the cellular neuron in association with the neuronal spike, the program instructions direct the computing apparatus to receive and process the neuronal signal in real-time to transfer the output data in real-time without off-line storage and processing of the neuronal signal.

\* \* \* \* \*